(12) United States Patent
Smith

(10) Patent No.: US 11,172,560 B2
(45) Date of Patent: Nov. 9, 2021

(54) OPHTHALMIC ILLUMINATION SYSTEM WITH CONTROLLED CHROMATICITY

(71) Applicant: NOVARTIS AG, Basel (CH)

(72) Inventor: Ronald T. Smith, Irvine, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 15/620,128

(22) Filed: Jun. 12, 2017

(65) Prior Publication Data

US 2018/0062344 A1 Mar. 1, 2018

Related U.S. Application Data

(60) Provisional application No. 62/379,469, filed on Aug. 25, 2016.

(51) Int. Cl.
| | | |
|---|---|---|
| A61B 3/00 | (2006.01) | |
| H05B 47/10 | (2020.01) | |
| G02B 27/10 | (2006.01) | |
| A61F 9/008 | (2006.01) | |
| G01J 1/42 | (2006.01) | |
| G01J 3/51 | (2006.01) | |
| G02B 27/14 | (2006.01) | |
| G01J 3/02 | (2006.01) | |

(52) U.S. Cl.
CPC ............ *H05B 47/10* (2020.01); *A61F 9/008* (2013.01); *G01J 1/4257* (2013.01); *G01J 3/513* (2013.01); *G02B 27/1006* (2013.01); *A61F 2009/00874* (2013.01); *G01J 3/0205* (2013.01); *G01J 3/0264* (2013.01); *G02B 27/141* (2013.01); *G02B 27/145* (2013.01)

(58) Field of Classification Search
CPC .... A61B 3/10; A61B 3/13; A61B 3/14; A61B 3/0025; A61B 3/0008; A61B 90/30
USPC ................................ 362/544, 277, 293, 221
See application file for complete search history.

(56) References Cited

U.S. PATENT DOCUMENTS

| | | |
|---|---|---|
| 3,026,449 A | 3/1962 | Rappaport |
| 4,222,375 A | 9/1980 | Martinez |
| 4,656,508 A | 4/1987 | Yokota |
| 4,870,952 A | 10/1989 | Martinez |

(Continued)

FOREIGN PATENT DOCUMENTS

| | | |
|---|---|---|
| EP | 1114608 B1 | 3/2003 |
| JP | 2006-87764 A | 4/2006 |

(Continued)

OTHER PUBLICATIONS

Abstract Only: Yasujima, H., et al. JP2006087764A; Publication Date Apr. 6, 2006; Machine translation; espacenet.com.

(Continued)

*Primary Examiner* — Rex R Holmes
*Assistant Examiner* — Sana Sahand

(57) ABSTRACT

An ophthalmic illumination system includes a broadband light source configured to emit a white laser beam, a first monochromatic light source configured to emit a first monochromatic laser beam having a first central wavelength, optics configured to receive a combined light beam comprising the white laser beam and the monochromatic laser, and a controller comprising a processor and a memory configured to control a chromaticity of the combined light beam by changing an output power of the first monochromatic light source.

16 Claims, 14 Drawing Sheets

(56) References Cited

U.S. PATENT DOCUMENTS

| | | |
|---|---|---|
| 4,883,333 A | 11/1989 | Yanez |
| 4,884,133 A | 11/1989 | Kanno et al. |
| 5,086,378 A | 2/1992 | Prince |
| 5,301,090 A | 4/1994 | Hed |
| 5,420,768 A | 5/1995 | Kennedy |
| 5,465,170 A | 11/1995 | Arimoto |
| 5,526,190 A | 6/1996 | Hubble, III et al. |
| 5,591,160 A | 1/1997 | Reynard |
| 5,598,042 A | 1/1997 | Mix et al. |
| 5,634,711 A | 6/1997 | Kennedy et al. |
| 5,657,116 A | 8/1997 | Kohayakawa |
| 5,736,410 A | 4/1998 | Zarling et al. |
| 5,830,139 A | 11/1998 | Abreu |
| 5,859,693 A | 1/1999 | Dunne et al. |
| 5,997,163 A | 12/1999 | Brown |
| 6,000,813 A | 12/1999 | Krietzman |
| 6,015,403 A | 1/2000 | Jones |
| 6,036,683 A | 3/2000 | Jean et al. |
| 6,102,696 A | 8/2000 | Osterwalder et al. |
| 6,120,460 A | 9/2000 | Abreu |
| 6,123,668 A | 9/2000 | Abreu |
| D434,753 S | 12/2000 | Druckenmiller et al. |
| 6,183,086 B1 | 2/2001 | Neubert |
| 6,190,022 B1 | 2/2001 | Tocci et al. |
| 6,211,626 B1 | 4/2001 | Lys et al. |
| 6,213,943 B1 | 4/2001 | Abreu |
| 6,217,188 B1 | 4/2001 | Wainwright et al. |
| 6,226,126 B1 | 5/2001 | Conemac |
| 6,268,613 B1 | 7/2001 | Cantu et al. |
| 6,270,244 B1 | 8/2001 | Naum |
| 6,272,269 B1 | 8/2001 | Naum |
| 6,336,904 B1 | 1/2002 | Nikolchev |
| 6,431,731 B1 | 8/2002 | Krietzman |
| 6,436,035 B1 | 8/2002 | Toth et al. |
| 6,459,844 B1 | 10/2002 | Pan |
| 6,606,332 B1 * | 8/2003 | Boscha ............... H04N 9/3129 348/750 |
| 6,730,940 B1 | 5/2004 | Steranka et al. |
| 6,786,628 B2 | 9/2004 | Steen et al. |
| 6,893,258 B1 | 5/2005 | Kert |
| 6,917,057 B2 | 7/2005 | Stokes et al. |
| 6,960,872 B2 | 11/2005 | Beeson et al. |
| 7,025,464 B2 | 4/2006 | Beeson et al. |
| 7,063,436 B2 | 6/2006 | Steen et al. |
| 7,229,202 B2 | 6/2007 | Sander |
| 7,276,737 B2 | 10/2007 | Camras et al. |
| 7,301,271 B2 | 11/2007 | Erchak et al. |
| 7,325,957 B2 | 2/2008 | Morejon et al. |
| 7,344,279 B2 | 3/2008 | Mueller et al. |
| 7,349,163 B2 | 3/2008 | Angelini et al. |
| 7,403,680 B2 | 7/2008 | Simbal |
| 7,482,636 B2 * | 1/2009 | Murayama ......... H01L 25/0753 257/98 |
| 7,494,228 B2 | 2/2009 | Harbers et al. |
| 7,556,412 B2 | 7/2009 | Guillermo |
| 7,561,329 B2 | 7/2009 | Zahniser et al. |
| 7,682,027 B2 | 3/2010 | Buczek et al. |
| 7,918,583 B2 | 4/2011 | Chakmakjian et al. |
| 7,990,587 B2 | 8/2011 | Watanabe |
| 8,223,447 B2 | 7/2012 | Artsyukhovich |
| 8,292,434 B2 | 10/2012 | Horvath et al. |
| 8,315,280 B2 | 11/2012 | Zimare et al. |
| 8,317,382 B2 | 11/2012 | Smith |
| 8,371,694 B2 | 2/2013 | Artsyukhovich |
| 8,371,695 B2 | 2/2013 | Papac et al. |
| 8,474,977 B2 | 7/2013 | Hahn et al. |
| 8,480,233 B2 | 7/2013 | Smith |
| 8,488,930 B2 | 7/2013 | Papac |
| 8,542,962 B2 | 9/2013 | Smith |
| 8,662,670 B2 | 3/2014 | Papac et al. |
| 8,992,021 B2 | 3/2015 | Smith |
| 9,055,885 B2 | 6/2015 | Horvath |
| 9,402,643 B2 | 8/2016 | Auld |
| 9,693,686 B2 | 7/2017 | Smith |
| 9,968,416 B2 | 5/2018 | Smith |
| 10,295,718 B2 | 5/2019 | Mirsepassi |
| 10,400,967 B2 | 9/2019 | Smith |
| 10,433,718 B2 | 10/2019 | Liolios |
| 10,441,157 B2 | 10/2019 | Smith |
| 10,507,074 B2 | 12/2019 | Smith |
| 10,537,401 B2 | 1/2020 | Dos Santos |
| 2001/0052930 A1 | 12/2001 | Adair et al. |
| 2002/0003928 A1 | 1/2002 | Bischel et al. |
| 2002/0087149 A1 | 7/2002 | McCary |
| 2002/0137984 A1 | 9/2002 | Chhibber et al. |
| 2002/0145776 A1 * | 10/2002 | Chow ................... H04B 10/69 398/212 |
| 2003/0112421 A1 | 6/2003 | Smith |
| 2003/0132701 A1 | 7/2003 | Sato et al. |
| 2003/0147254 A1 | 8/2003 | Yoneda et al. |
| 2003/0169603 A1 | 9/2003 | Luloh et al. |
| 2003/0223248 A1 | 12/2003 | Cronin et al. |
| 2003/0223249 A1 | 12/2003 | Lee et al. |
| 2004/0004846 A1 | 1/2004 | Steen et al. |
| 2004/0090796 A1 | 5/2004 | Steen et al. |
| 2004/0124429 A1 | 7/2004 | Stokes et al. |
| 2004/0233655 A1 | 11/2004 | Zimmerman et al. |
| 2005/0018309 A1 | 1/2005 | McGuire, Jr. et al. |
| 2005/0024587 A1 | 2/2005 | Somani |
| 2005/0047172 A1 | 3/2005 | Sander |
| 2005/0063171 A1 | 3/2005 | Leitel et al. |
| 2005/0099824 A1 | 5/2005 | Dowling et al. |
| 2005/0110808 A1 | 5/2005 | Goldschmidt et al. |
| 2005/0140270 A1 | 6/2005 | Henson et al. |
| 2005/0171416 A1 * | 8/2005 | Proniewicz ........ A61B 5/14532 600/319 |
| 2005/0190562 A1 | 9/2005 | Keuper et al. |
| 2005/0243539 A1 | 11/2005 | Evans et al. |
| 2005/0270775 A1 | 12/2005 | Harbers et al. |
| 2006/0203468 A1 | 9/2006 | Beeson et al. |
| 2006/0262272 A1 | 11/2006 | Anderson et al. |
| 2007/0102033 A1 | 5/2007 | Petrocy |
| 2007/0133211 A1 | 6/2007 | Yoneda et al. |
| 2007/0213618 A1 | 9/2007 | Li et al. |
| 2007/0219417 A1 | 9/2007 | Roberts et al. |
| 2007/0273290 A1 * | 11/2007 | Ashdown ............. F21V 29/004 315/113 |
| 2007/0284597 A1 | 12/2007 | Nawashiro et al. |
| 2007/0291491 A1 | 12/2007 | Li et al. |
| 2008/0030984 A1 | 2/2008 | Harbers et al. |
| 2008/0073616 A1 | 3/2008 | Dong et al. |
| 2008/0112153 A1 | 5/2008 | Iwasaki et al. |
| 2008/0144169 A1 | 6/2008 | Zahniser et al. |
| 2008/0175002 A1 | 7/2008 | Papac et al. |
| 2008/0208006 A1 | 8/2008 | Farr |
| 2008/0246919 A1 | 10/2008 | Smith |
| 2008/0246920 A1 * | 10/2008 | Buczek ................. A61B 90/36 351/221 |
| 2008/0262316 A1 | 10/2008 | Ajima et al. |
| 2008/0291682 A1 | 11/2008 | Falicoff et al. |
| 2009/0036955 A1 | 2/2009 | Han |
| 2009/0054957 A1 | 2/2009 | Shanbaky |
| 2009/0092750 A1 | 4/2009 | Yang et al. |
| 2009/0095960 A1 | 4/2009 | Murayama |
| 2009/0105698 A1 | 4/2009 | Hodel et al. |
| 2009/0131823 A1 | 5/2009 | Andreyko et al. |
| 2009/0154137 A1 | 6/2009 | Bierhuizen et al. |
| 2009/0154192 A1 | 6/2009 | Krattiger |
| 2009/0168395 A1 | 7/2009 | Mrakovich et al. |
| 2009/0182313 A1 | 7/2009 | Auld |
| 2009/0190371 A1 | 7/2009 | Root et al. |
| 2009/0203966 A1 | 8/2009 | Mizuyoshi |
| 2009/0219586 A1 | 9/2009 | Fujimoto et al. |
| 2009/0227847 A1 | 9/2009 | Tepper et al. |
| 2009/0267088 A1 | 10/2009 | Peng et al. |
| 2010/0100006 A1 | 4/2010 | Xu et al. |
| 2010/0127299 A1 | 5/2010 | Smith et al. |
| 2010/0157620 A1 * | 6/2010 | Bhadri ...................... A61B 3/13 362/554 |
| 2010/0182569 A1 | 7/2010 | Artsyukhovich et al. |
| 2010/0228089 A1 | 9/2010 | Hoffman et al. |
| 2010/0261966 A1 * | 10/2010 | Reimer ............... A61B 1/0646 600/160 |
| 2010/0317923 A1 | 12/2010 | Endo et al. |

(56) References Cited

U.S. PATENT DOCUMENTS

| | | | |
|---|---|---|---|
| 2011/0009752 A1 | 1/2011 | Chen et al. | |
| 2011/0037948 A1* | 2/2011 | Horvath | A61B 1/0653 351/221 |
| 2011/0037949 A1 | 2/2011 | Papac et al. | |
| 2011/0038174 A1 | 2/2011 | Papac et al. | |
| 2011/0044701 A1* | 2/2011 | Schenk | H05B 37/02 398/183 |
| 2011/0122366 A1 | 5/2011 | Smith | |
| 2011/0149246 A1* | 6/2011 | Artsyukhovich | A61B 3/0008 351/221 |
| 2011/0149247 A1* | 6/2011 | Artsyukhovich | A61B 3/0008 351/221 |
| 2011/0149591 A1 | 6/2011 | Smith | |
| 2011/0149592 A1 | 6/2011 | Artsyukhovich | |
| 2011/0292343 A1* | 12/2011 | Papac | G02B 27/141 351/221 |
| 2011/0292344 A1* | 12/2011 | Papac | A61B 3/0008 351/221 |
| 2012/0075601 A1* | 3/2012 | Den Boef | G01N 21/47 355/67 |
| 2012/0169995 A1* | 7/2012 | Mohr | A61B 3/12 351/206 |
| 2014/0217924 A1* | 8/2014 | Sato | G09G 3/3233 315/294 |
| 2016/0128557 A1 | 5/2016 | Papac et al. | |
| 2016/0346058 A1 | 12/2016 | Bacher | |
| 2017/0356608 A1 | 12/2017 | Smith | |

FOREIGN PATENT DOCUMENTS

| | | | |
|---|---|---|---|
| JP | 2006-318773 A | | 11/2006 |
| JP | 2015004902 A | * | 1/2015 |
| WO | 00/54655 A1 | | 9/2000 |
| WO | 2008/133736 A2 | | 11/2008 |

OTHER PUBLICATIONS

Liu, C.K., et al.; "High Efficiency Silicon-Based High Power LED Package Integrated with Micro-Thermoelectric Device"; Microsystems Packaging, Assembly and Circuits Technology, pp. 29-33; 2007 Taipei Conference; IMPACT 2007; worlwide web: www.ieee.org; DOI 10.1109/IMPACT.2007.4433562.

PCT/US2012/052200 International Search Report dated Oct. 26, 2012.

* cited by examiner

OPHTHALMIC ILLUMINATION SYSTEM WITH CONTROLLED CHROMATICITY

FIELD

This present disclosure relates generally to ophthalmic illuminators. More particularly, the present disclosure relates to devices, systems, and methods of controlling chromaticity of ophthalmic illumination systems.

BACKGROUND

Ophthalmic microsurgical procedures frequently require precision cutting and/or removing of various eye tissues. During such surgical procedures, proper illumination of the eye is important, and ophthalmic illumination systems are typically used to illuminate to the surgical field. A user, such as a surgeon or other medical professional, may insert an illumination probe into the eye to illuminate the inside of the eye for a procedure. Typically, the probe is connected to an optical port of an ophthalmic illumination system. The ophthalmic illumination system, which may be housed in a surgical console, includes a light source. The illumination system may also include other optical elements, such as collimating and condensing optics, that facilitate transmission of a light beam generated by the light source into an optical fiber extending into the probe.

During design and assembly of the ophthalmic illumination system, manufacturers seek to optimize various parameters and characteristics of the light beam, including chromaticity. Unfortunately, the chromaticity of a light beam generated by a light source, such as a supercontinuum laser engine, may not be initially calibrated as desired and tends to change with time. Such chromaticity shifts may adversely impact the surgeon's view of the surgical field, and could elevate the risk of phototoxicity in some cases. Accordingly, a need exists for improved illuminator systems that can accurately and efficiently configure, control, and maintain chromaticity over time.

SUMMARY

In general, the present disclosure relates to an ophthalmic illumination system with controlled chromaticity.

According to certain embodiments, an ophthalmic illumination system includes a broadband light source configured to emit a white laser beam, a first monochromatic light source configured to emit a first monochromatic laser beam having a first central wavelength, optics configured to receive a combined light beam comprising the white laser beam and the monochromatic laser, and a controller comprising a processor and a memory configured to control a chromaticity of the combined light beam by changing an output power of the first monochromatic light source.

In some examples, the controller is configured to change the output power of the first monochromatic light source based on an operating time of the broadband light source.

The ophthalmic illumination system may also include a plurality of chromaticity sensors configured to measure a chromaticity of the combined light beam. The controller may be configured to receive a signal from the chromaticity sensors indicating a measured chromaticity of the combined light beam, determine that the measured chromaticity is not within a target chromaticity range, calculate an output power adjustment for the first monochromatic light source that will modify chromaticity of the combined light beam to fall within the target chromaticity range, and generate a signal to change the output power of the first monochromatic light source, based on the calculated output power adjustment.

Certain embodiments include a sleeve configured to optically combine the white laser beam with the first monochromatic laser beam. Other embodiments include a dielectric filter configured to spectrally combine the white laser beam with the first monochromatic laser beam.

In some instances, the ophthalmic illumination system includes a second monochromatic light source configured to emit a second monochromatic laser beam having a second central wavelength. The combined light beam received by the optics may include the white laser beam, the first monochromatic laser beam, and the second monochromatic laser beam, and the controller may be configured to control the chromaticity of the combined light beam by changing the output power of the first monochromatic light source or the second monochromatic light source.

Certain embodiments disclose a method that includes generating white laser beam with a broadband light source, generating a first monochromatic laser beam having a first central wavelength with a first monochromatic light source, receiving a combined light beam comprising the white laser beam and the monochromatic laser with receiving optics, and controlling chromaticity of the combined light beam by changing an output power of the first monochromatic light source.

The method may include changing the output power of the first monochromatic light source based on an operating time of the broadband light source.

In some embodiments, the method includes measuring the chromaticity of the combined light beam using a plurality of chromaticity sensors, determining that the measured chromaticity is not within a target chromaticity range, calculating an output power adjustment for the monochromatic light source that will modify chromaticity of the combined light beam to fall within the target chromaticity range, and generating a signal to change the output power of the first monochromatic light source, based on the calculated output power adjustment.

In particular examples, the method may include optically combining the white laser beam with the first monochromatic laser beam with a sleeve or spectrally combining the white laser beam with the first monochromatic laser beam with a dielectric filter.

Certain methods include generating a second monochromatic laser beam having a second central wavelength with a second monochromatic light source and controlling the chromaticity of the combined light beam by changing the output power of the first monochromatic light source or the second monochromatic light source. The combined light beam may comprise the white laser beam, the first monochromatic laser beam, and the second monochromatic laser beam.

Certain embodiments may provide one or more technical advantages. For example, embodiments of the present disclosure may provide an improved view of a surgical field by optimizing and maintaining the chromaticity of a light source. This can be particularly beneficial over the life of a supercontinuum laser, which tends to shift toward red or blue over time. Further, certain embodiments may reduce risk of phototoxicity induced by overexposure to blue light during retinal procedures.

BRIEF DESCRIPTION OF THE DRAWINGS

For a more complete understanding of the present disclosure and the advantages thereof, reference is now made to

Figure 1A:
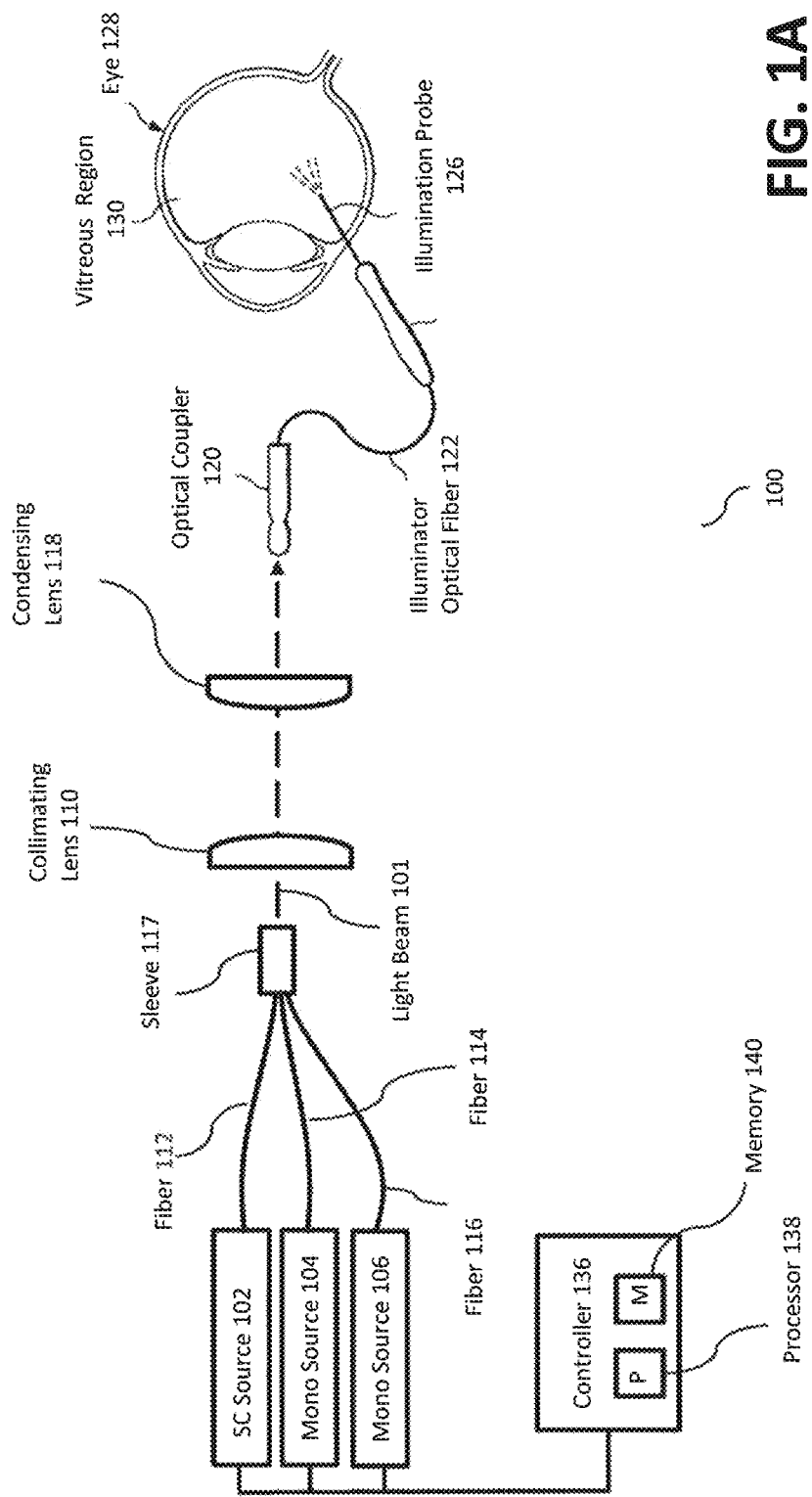
Figure 1B:
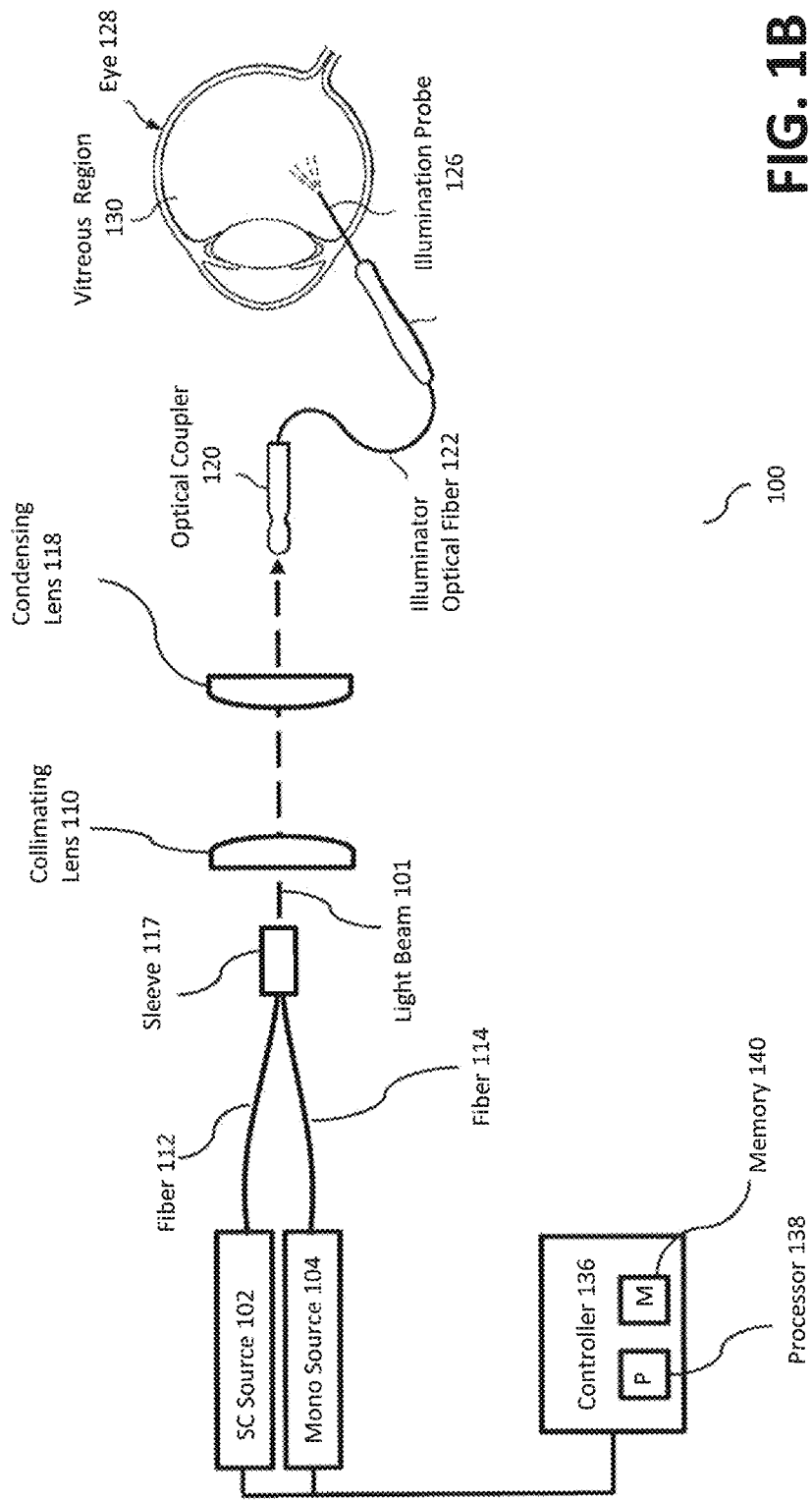
Figure 1C:
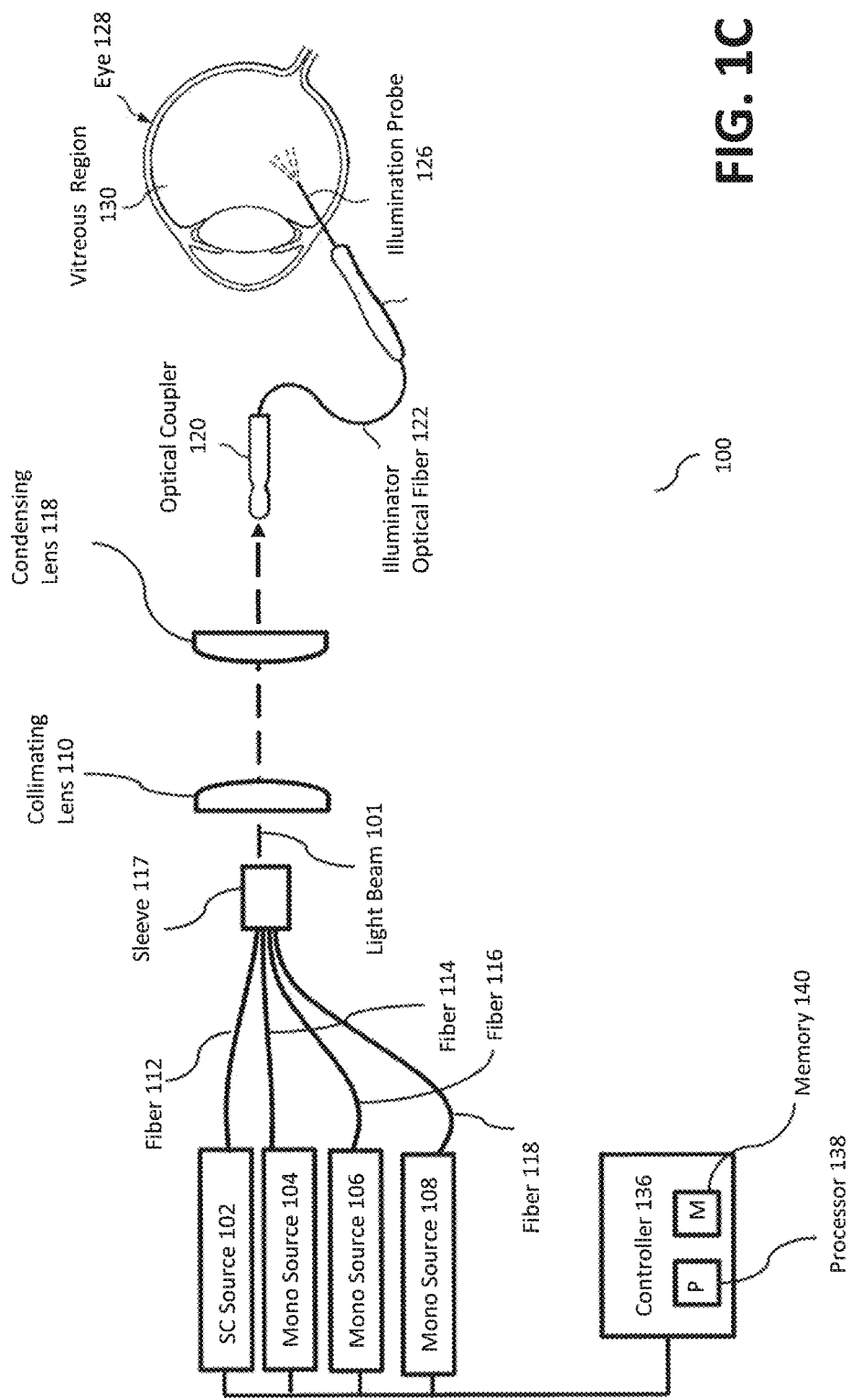

3 the following description taken in conjunction with the accompanying drawings in which like reference numerals indicate like features and wherein:

FIGS. 1A-1C illustrate example ophthalmic illumination systems operable to control chromaticity of a light beam, according to certain embodiments.

Figure 2:
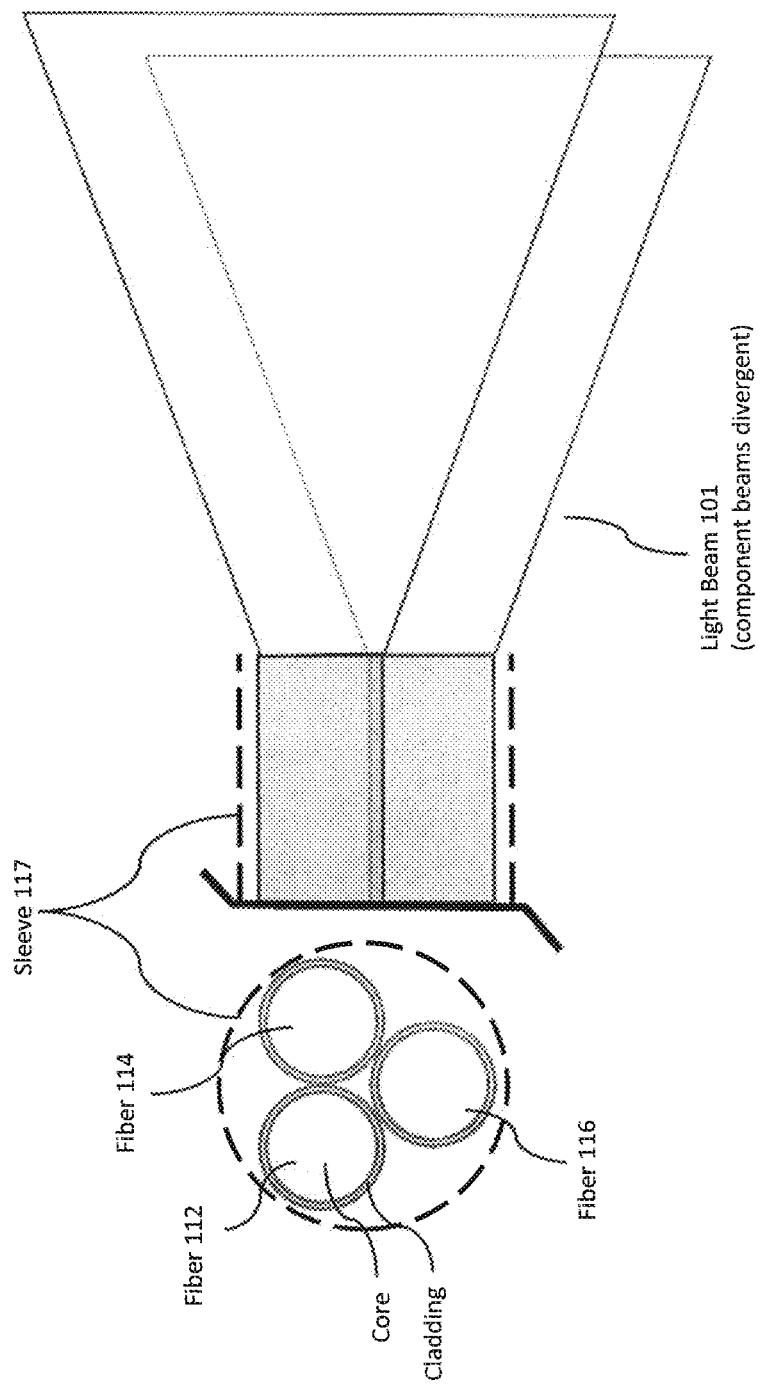
Figure 3:
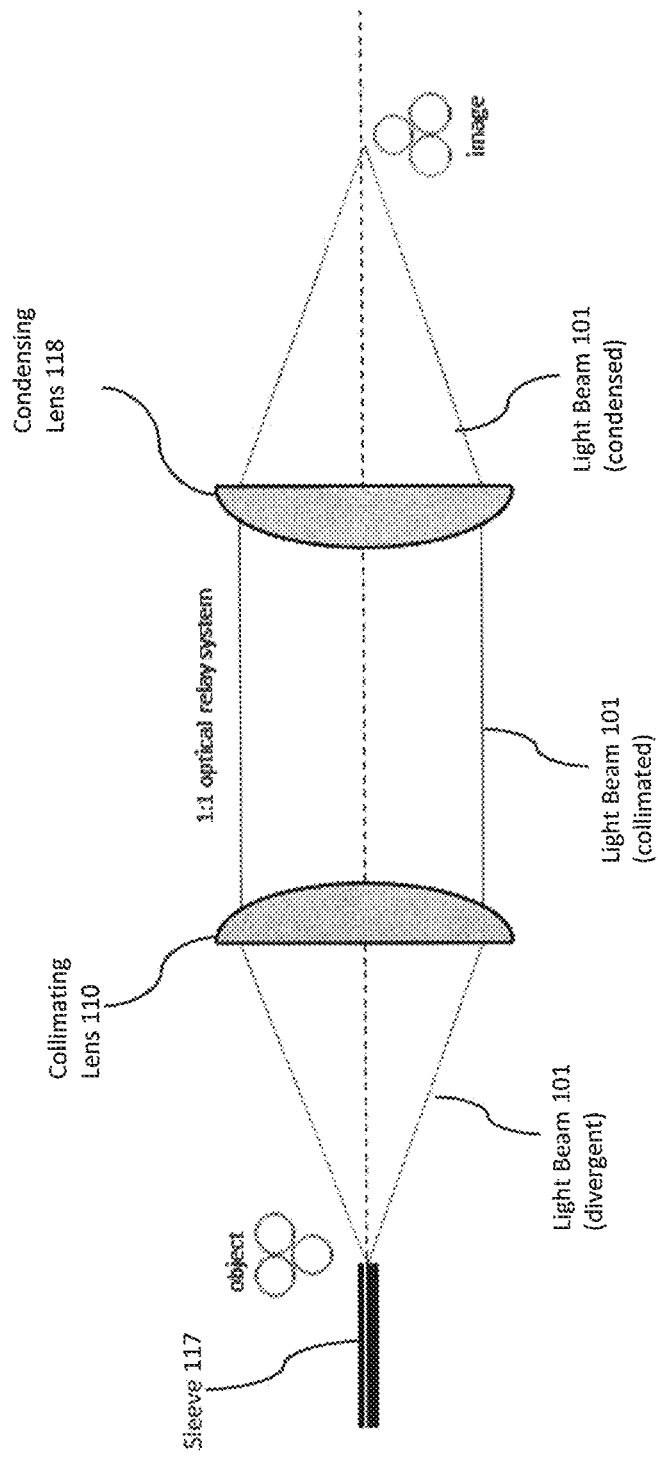

FIGS. 2 and 3 illustrate aspects of the example ophthalmic illumination systems depicted in FIGS. 1A-1C.

Figure 4:
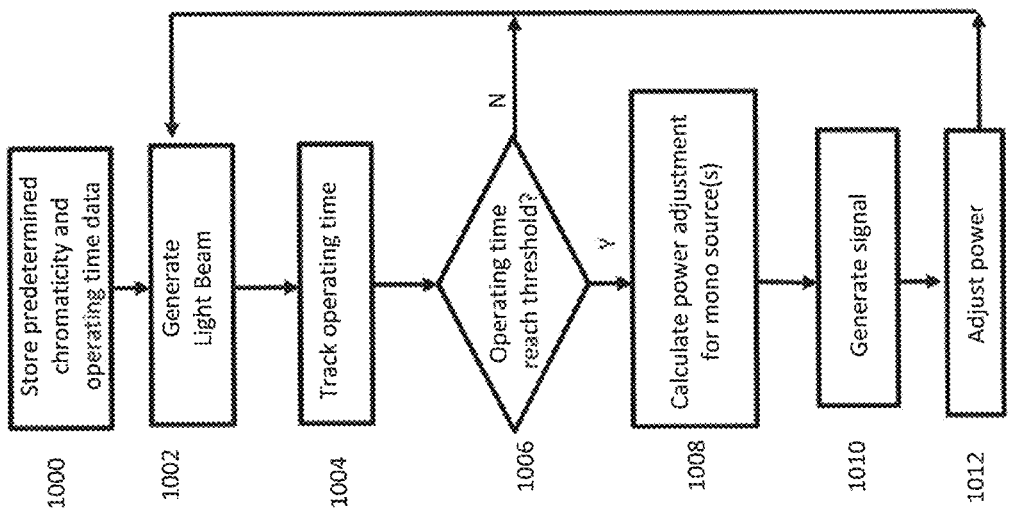

FIG. 4 illustrates a method for controlling chromaticity of a light beam based on pre-stored data, according to certain embodiments.

Figure 5:
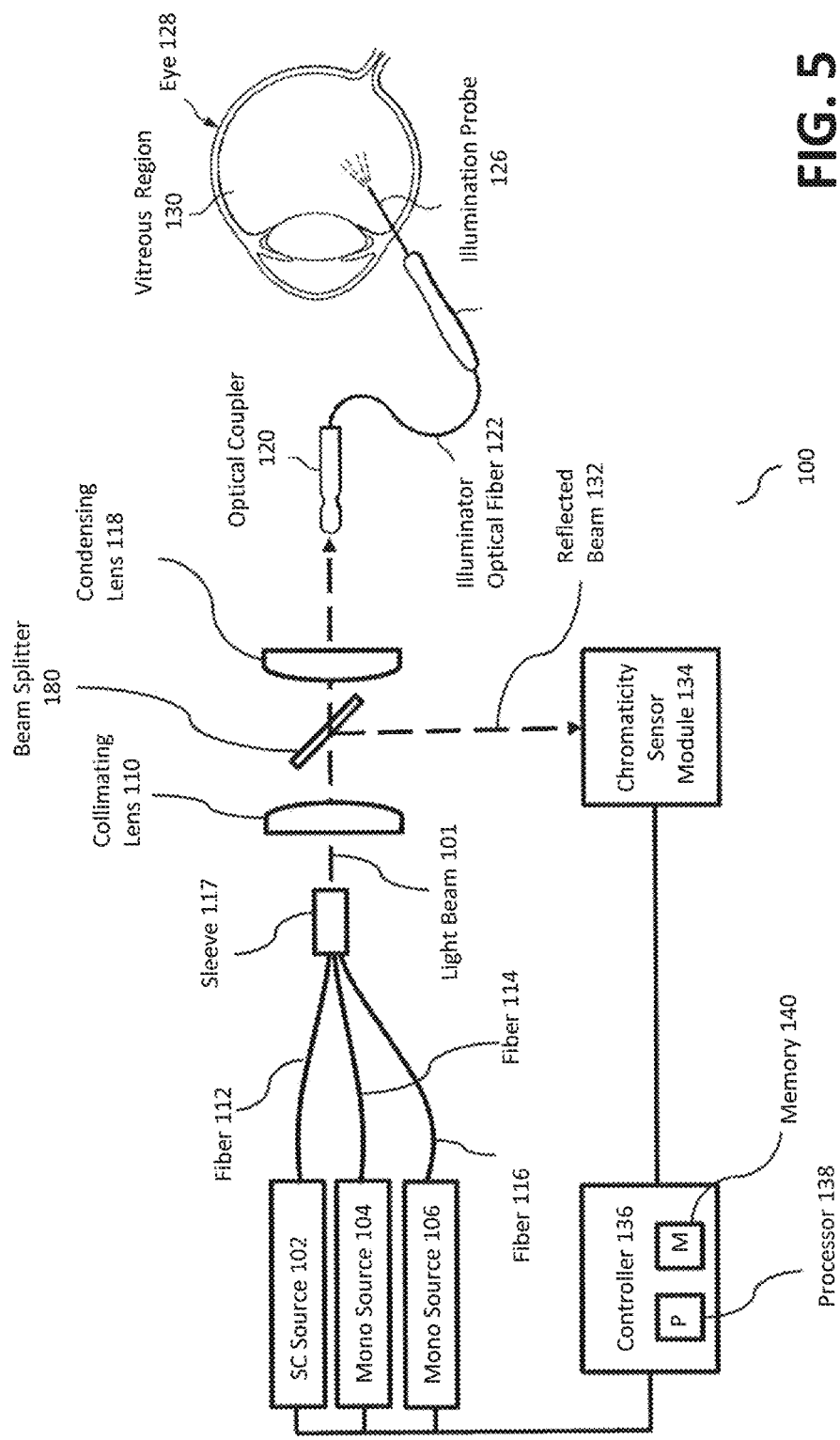

FIG. 5 illustrates example ophthalmic illumination systems operable to control chromaticity of a light beam using a chromaticity sensor module, according to certain embodiments.

Figure 6:
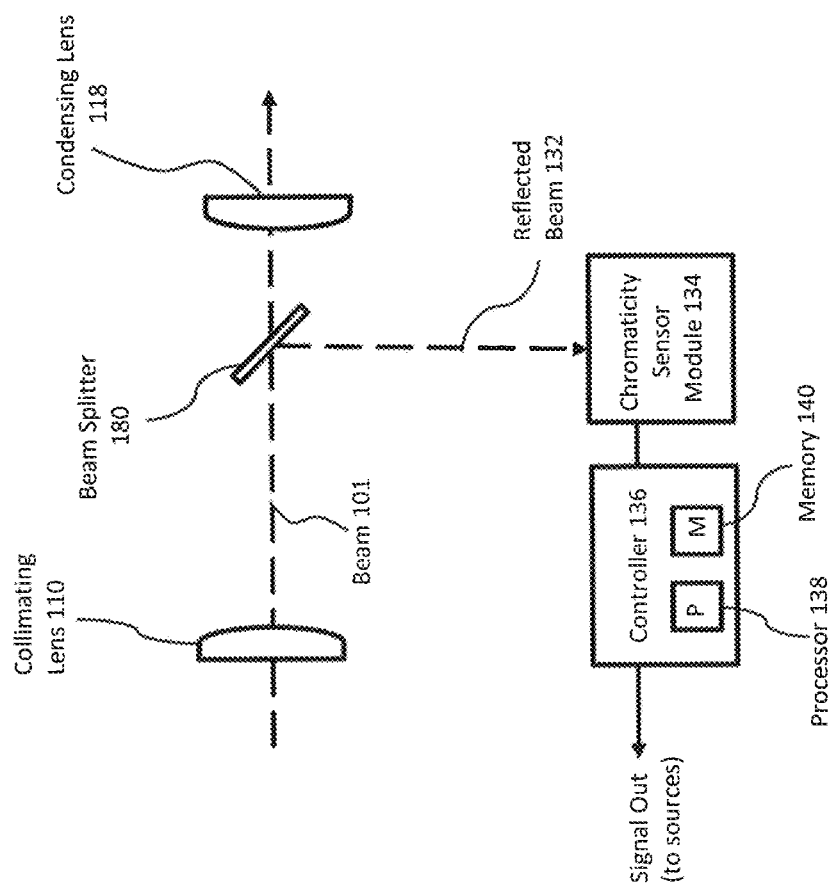
Figure 7:
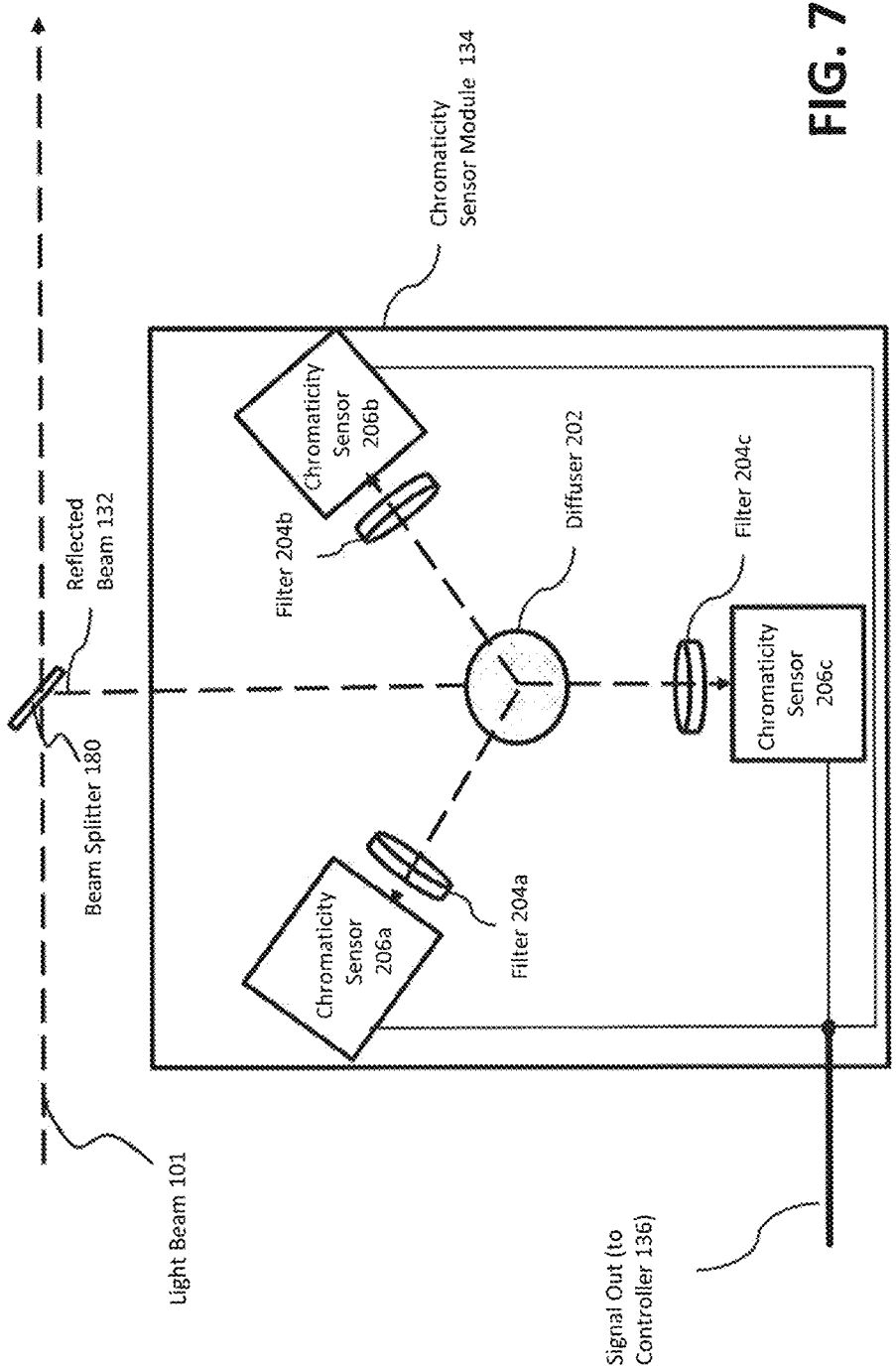

FIGS. 6-7 illustrate aspects of an example chromaticity sensor module in additional detail.

Figure 8:
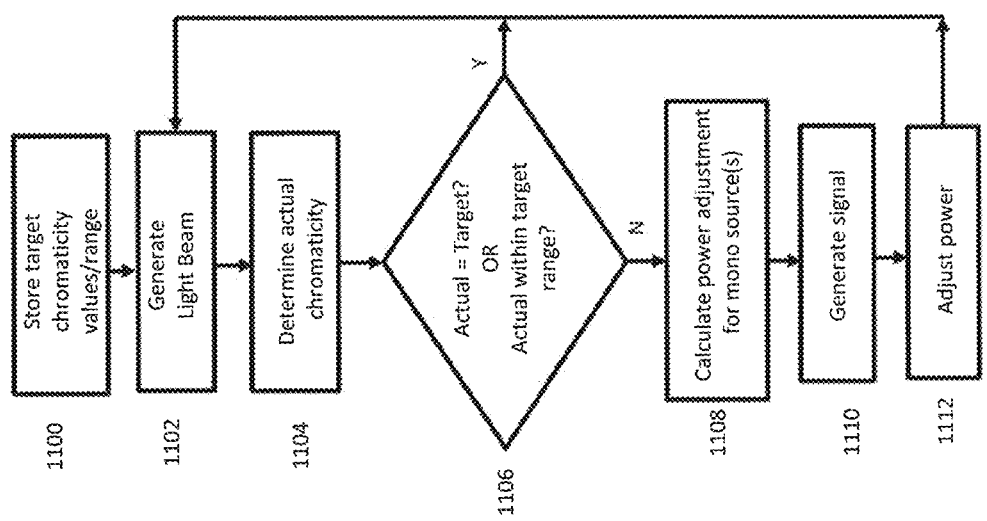

FIG. 8 illustrates a method for controlling chromaticity of a light beam based on real-time chromaticity measurements, according to certain embodiments.

Figure 9A:
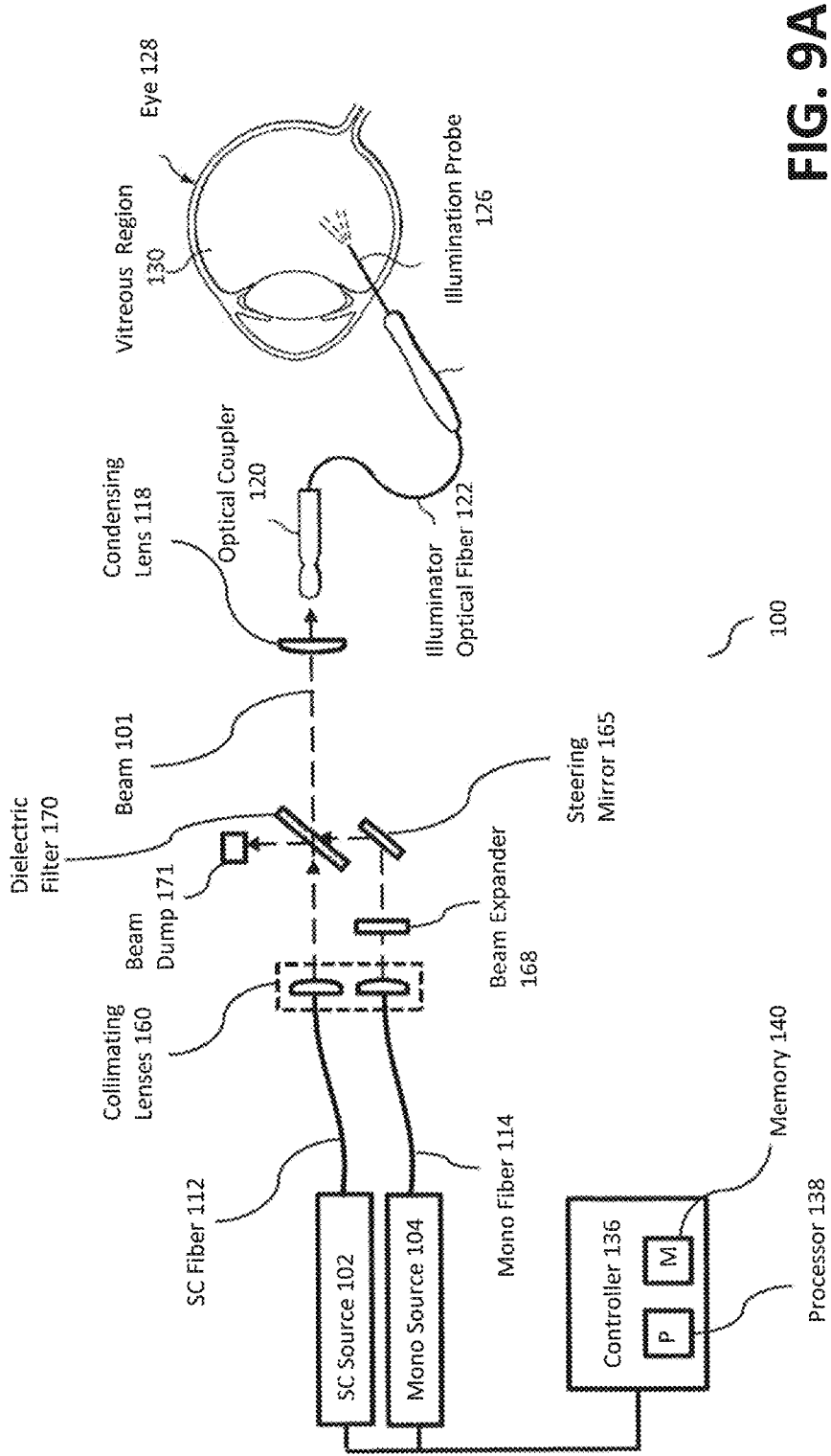
Figure 9B:
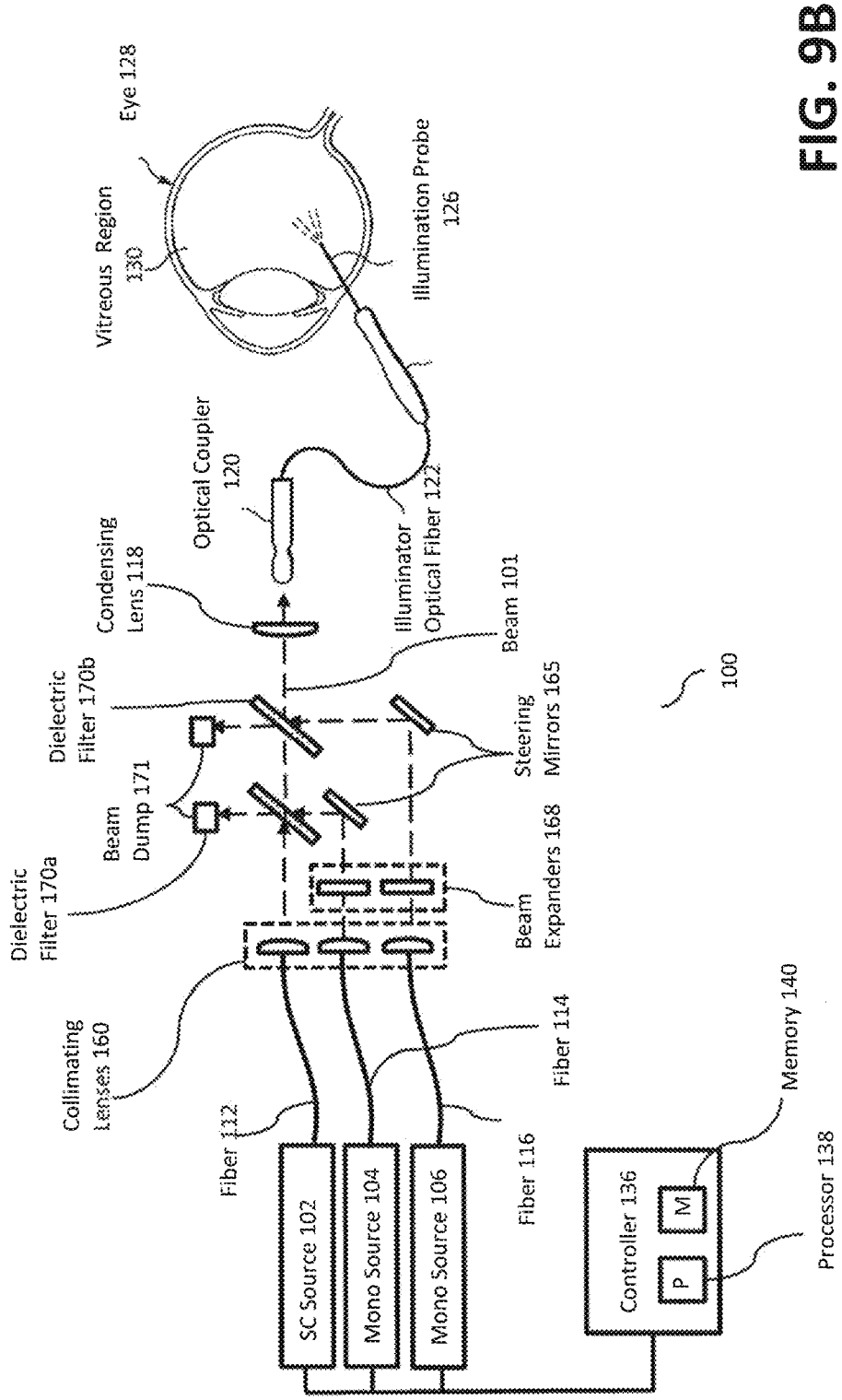

FIGS. 9A and 9B illustrate example ophthalmic illumination systems operable to control chromaticity of a light beam, according to certain embodiments.

Figure 10:
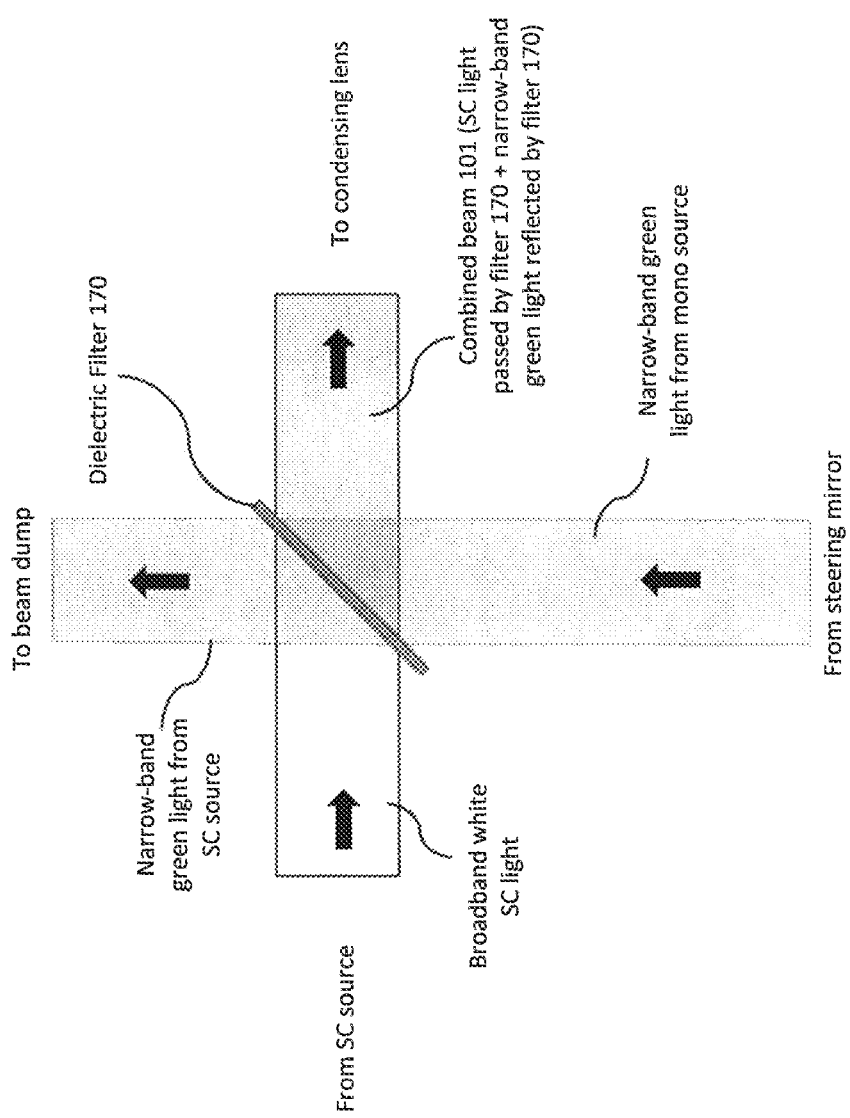

FIG. 10 illustrates illustrate aspects of the example ophthalmic illumination systems depicted in FIGS. 9A and 9B.

Figure 11:
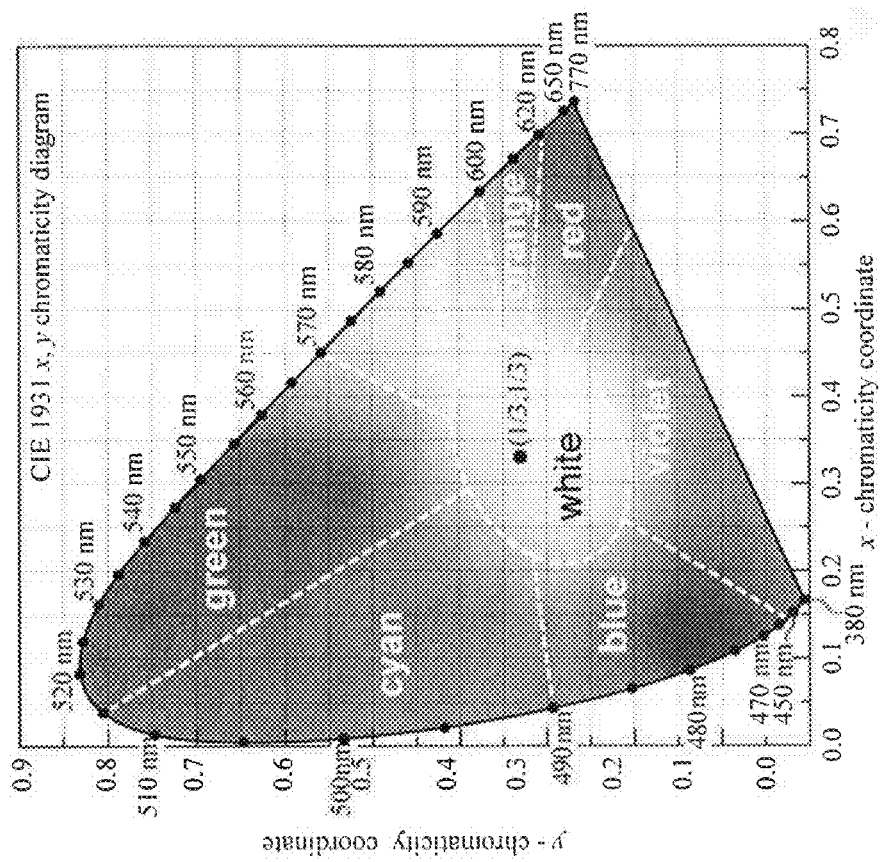

FIG. 11 illustrates a chromaticity diagram.

One skilled in the art will appreciate that the drawings, described below, are for illustration purposes only and do not limit the scope of the disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. Further, in some instances the same reference numbers are used throughout the drawings to refer to the same or like parts.

In general, the present disclosure relates to illumination systems for ophthalmic surgery, including vitrectomies. Often, the chromaticity of supercontinuum white lasers used in vitrectomy surgery changes (shifting either redder or bluer) with operating time. The present disclosure describes techniques for optically combining a white SC laser beam with a blue, green, and/or red laser beam to compensate for chromaticity shifts and maintain a constant chromaticity over the lifetime of the illumination system.

FIGS. 1A-1C illustrate an example illumination system 100 operable to control the chromaticity of a light source, according to certain embodiments. In particular, system 100 of FIG. 1A-C includes a supercontinuum (SC) light source 102 operable to generate an SC laser beam and direct the beam toward fiber 112, which transmits the SC beam. System 100 also includes monochromatic light sources (e.g.,

4

104, 106, 108) each of which generates substantially monochromatic laser beams (of the same or different chromaticity) and directs the beams toward fibers (e.g., 114, 116, 118) respectively, which transmit the monochromatic beams. Fibers 112, 114, 116, and 118 are coupled with a sleeve 117 which physically brings the fibers (and the beams transmitted therein) very close together to combine them optically. Thus, optically combined light beam 101 exiting sleeve 117 comprises a plurality of closely-spaced beams of light—one or more monochromatic beams and a SC beam—which are transmitted toward an achromatic collimating lens 110. The beams are collimated by collimating lens 110 and remain very close as they propagate toward condensing lens 118, which condenses the beams so they may be delivered into an optical coupler 120. Optical coupler 120 receives condensed beam 101 and transmits it through an illuminator fiber 122 to an illumination probe 126, which may be inserted in an eye 128 to illuminate a vitreous region 130. Controller 136 comprises a processor 138 and memory 140 configured to execute software instructions or otherwise control SC source 102, mono source 104, mono source 106, and mono source 108.

In certain examples, SC source 102 comprises an SC laser that generates a broad continuous spectra laser beam (e.g., between approximately 400 nm and 1700 nm). In certain embodiments, SC source 102 generates a white supercontinuum laser beam emitted at a calibrated chromaticity. SC source 102 may be calibrated at the time of manufacture to emit a light beam at a target chromaticity. If the chromaticity is not as desired, it may be set to or maintained at a target chromaticity by combining the light beam with beams generated by one or more monochromatic sources, as described herein. In certain embodiments, the target chromaticity is white or substantially achromatic. In other embodiments, the target chromaticity may correspond to a particular color.

Monochromatic ("mono") sources 104, 106, and 108 each comprise a light source that generates a substantially monochromatic beam of light, such as a monochromatic blue, green, or red laser. The example of FIG. 1A include two monochromatic light sources in addition to the SC laser source. According to the present disclosure, a monochromatic source may comprise any of the following:

- a green laser having central wavelength in the range of 510 to 550 nm, and in particular a central wavelength of 532 nm.
- a violet or blue laser having central wavelength in the range of 440 to 490 nm, and in particular a central wavelength of 460 nm.
- a red laser having a central wavelength in the range of 610 to 670 nm, and in particular a central wavelength of 635 nm.

Various embodiments may include one, two, three, or more monochromatic sources having any of the characteristics descried herein.

The example shown in FIG. 1B includes only a one monochromatic source 104. In various embodiments, source 104 may be a red, blue, or green laser. The example shown in FIG. 1C includes three monochromatic sources. In various embodiments, sources 104, 106, and 108 may be red, blue, and green lasers, respectively.

In various embodiments of system 100, monochromatic light sources 104-108 may be any suitable light sources for producing a light beam with suitable spectral characteristics, including but not limited to a gas laser, dye laser, metal vapor laser, solid state laser, semiconductor laser, fiber laser, halogen tungsten lamp, high pressure arc lamp, light emitting diode (LED), super-luminescent diode, etc.

Fibers 112, 114, 116, and 118 are optical fibers that operate as a waveguide to transmit light from sources 102, 104, 106, and 108 respectively. Optical fibers 112, 114, 116, and 118 may each include an optically transmissive fiber optic core surrounded by a cladding material having a generally low index of refraction relative to the fiber core. The fiber optic core may be made of various materials, including but not limited to glass and plastics. Optical fibers 112, 114, 116, and 118 may include additional layers depending on the requirements of a particular application. For example, the optical fibers may include a buffer material encasing cladding material, as well as an outer protective jacket (such as a plastic or metal tube) for shielding the cable's interior components from damage. Each of optical fibers 112, 114, 116, and 118 may comprise one or more multimode fibers. Optical fibers have a fiber axis that is typically the optical axis of the fiber core.

In various examples, it is important that, after collimation, the beam diameter of the monochromatic laser beam is the same as the beam diameter of the white SC laser beam. This ensures that the SC white beam and the monochromatic beams focusing into and exiting out of the illuminator fiber have angular spreads essentially equal to one another, thereby eliminating the possibility of chromaticity variations with exit angle from the multimode fiber. Various techniques may be employed to achieve the desired equal beam diameters. In one example, the focal length of the collimating lens which collimates the beam diverging from a monochromatic source is selected so that the diameter of the collimated monochromatic beam matches the diameter of the collimated white SC beam. In another example, light from the monochromatic source(s) may be coupled in free space into a single mode fiber custom-designed to have a mode field diameter at the monochromatic wavelength such that the beam exiting the fiber has the desired beam numerical aperture (NA). Thus, in certain embodiments, fibers 114, 116, and 118 may comprise a fiber with such characteristics. Additionally or alternatively, certain examples may include optics to expand or condense component monochromatic light beams to the desired diameter.

In certain examples, sleeve 117 is a suitably-sized tube which physically couples fibers 112, 114, 116, and/or 118 to bundle them together and bring light beams transmitted therein close together. Sleeve 117 may be made of any suitable material, including but not limited to a polymer (e.g., plastic).

FIG. 2 illustrates aspects of sleeve 117 in additional detail, according to certain embodiments. As shown in FIG. 2, fibers 112, 114, and 116 may be arranged such that, within sleeve 117, an outer jacket layer of each fiber (not shown) is not present. Accordingly, fibers 112, 114, and 116 include only core and cladding within at least a portion of sleeve 117 (preferably near the exit). This allows the core of fibers 112, 114, and 116 to be brought into close proximity, which likewise brings the light transmitted in each fiber into close proximity. Accordingly, light beam 101 (here, the combined beams of sources 102, 104, and 106) may comprise a triad of individual light beams exiting fibers 112, 114 and 117 at a distal end of sleeve 117. In embodiments that include three monochromatic sources, the fibers may be aligned such that the combined beam 101 includes a quad of individual beams when exiting the sleeve; in embodiments with a single monochromatic source, combined beam 101 includes a pair of individual beams.

In certain examples, the core diameter of each fiber 112, 114, 116, and 118 is under 10 µm (e.g., 8 µm), and the outer diameter of the cladding is under 12 µm (e.g., 10 µm). The core diameter of a typical consumable illuminator fiber 122 is approximately 77.5 µm and, taking tolerances into account, the core diameter of such an illuminator fiber will be at least approximately 59.5 µm at any given point. Thus, fibers 112, 114, and 116 arranged as described above (triad with core and cladding only) may be encompassed within a sleeve 117 having an inner diameter of less than 30 µm, and the combined light beam 101 exiting therefrom may readily be focused into the core of a 59.5 µm tolerance core diameter of an illuminator fiber. Even in a quad arrangement with an additional light source and fiber would readily fit within a 40 µm sleeve and the exiting beams may be directed into the core of a consumable fiber.

As shown in FIG. 2, the individual components of light beam 101 may be somewhat divergent as the light exits a distal end of sleeve 117. Diverging light exiting sleeve 117 may be collimated by collimating lens 110. Collimating lens 110 is configured to collimate light beam 101 (here comprising the beams produced by light sources 102, 104, and 106). Collimation of light involves aligning light rays such that they are substantially parallel. Collimating lens 110 may be any suitable lens or combination of lenses for collimating light beam 101.

Accordingly, the rays of light beam 101 exiting collimating lens 110 are substantially parallel, and are subsequently condensed by condensing lens 118. Condensing lens 118 focuses light beam 101 so that it can be directed into a small diameter optical fiber such as illuminator fiber 122. Condensing lens 118 is a lens of suitable configuration for the system and may be a biconvex or plano-convex spherical or aspheric lens in certain examples. In a plano-convex aspheric lens, one surface is planar and the other surface is convex with a precise aspheric surface in order to focus the light to a minimum diameter spot. Condensing lens 118 may comprise one or more lenses suitable for focusing light beam 101 into optical coupler 120.

Collimating lens 110 and condensing lens 118 may be identical and comprise a 1:1 optical relay system, as shown in FIG. 3. Here, the image at the focal point of condensing lens 118 (on the right of FIG. 3) corresponds to the object exiting sleeve 117, inverted at a 1:1 magnification (no change in size). In other examples, collimating lens 110 and condensing lens 118 may comprise an optical relay system that generates a magnified or de-magnified image (enlarged or reduced in size with respect to the object) suitable for transmission into optical coupler 120 and through illuminator fiber 122. Such may be useful in embodiments in which a particular cone angle is desired, as smaller spot sizes will yield a larger cone angle and vice-versa.

Optical coupler 120 receives light beam 101 from condensing lens 118 and transmits light beam 101 through illuminator optical fiber 122 and illumination probe 126. Optical coupler 120 may include any suitable components to facilitate transmission of light beam 101 into optical fiber 122.

Optical fiber 122 may include a flexible configuration to allow generally unimpeded manipulation of illumination probe 126. Optical fiber 122 may include an optically transmissive fiber optic core surrounded by a cladding material having a generally low index of refraction relative to the fiber optic core. The fiber optic core may be made of various materials, including but not limited to, glass and plastics. Optical fiber 122 may also include additional layers depending on the requirements of a particular application.

For example, optical fiber 122 may include a buffer material encasing cladding material, as well as an outer protective jacket (such as a plastic or metal tube) for shielding the cable's interior components from damage. Optical fiber 122 may comprise a multimode fiber, and may be consumable.

In certain embodiments, beam 101 is focused to a small spot size for delivery to optical fiber 122. In such embodiments, optical fiber 122 may be a nano-scaled fiber optic cable. Nano-scale optic fibers generally have a diameter (or other largest cross-sectional dimension) of less than 100 microns. When employed as fiber optic core of optical fiber 122 and illumination probe 126, the small diameter of nano-scale optic fiber may enable a reduction in the cross-sectional area of probe 126, which in turn may reduce the size of the surgical incision in sclera eye 128 through which probe 126 is inserted. Depending on the size of optical fiber 122, the incision may be small enough to render the resulting wound substantially self-healing, thereby eliminating the need to employ additional procedures to close the incision, such as sutures. Additionally, due to the small size of nano-scale optic fibers, it may be possible to integrate illumination probe 126 with another surgical instrument, such as an infusion cannula (not shown), to reduce the number of surgical incision required for inserting surgical instruments during a vitreoretinal procedure.

Optical fiber 122 extends to and through illumination probe 126 to transmit light beam 101 into eye 128. Probe 126 may comprise a hand piece held by the surgeon to allow manipulation of probe 126 in eye 128. As shown in FIG. 1, probe 126 may be inserted in eye 128 through an incision in the pars plana region, and may be positioned to illuminate the inside or vitreous region 130 of eye 128 during an ophthalmic surgical procedure. Light beam 101 carried by optical fiber 122 through illumination probe 126 are backscattered against interior surfaces of eye 128, illuminating the surgical site.

As noted above, the core diameter of a typical consumable illuminator fiber 122 may be approximately 77.5 µm. In certain examples, the core diameter and cladding thickness of fibers 112, 114, and 116 may cumulatively be small enough that a triad arrangement of fibers (or couplet or quad arrangements if fewer or additional mono sources and attendant fibers are included in the system) may be encompassed within sleeve 117 having an inner diameter that is smaller than the guaranteed minimum inner diameter of a consumable illuminator fiber (e.g., 59.5 µm, taking tolerances into account).

Controller 136 may be communicatively coupled to each light source (e.g., SC source 102, mono sources 104, 106, and 108) via a wired or wireless connection 142 and may include any suitable combination of hardware, firmware, and software. In particular, processor 138 may include one or more microprocessors, field-programmable gate arrays (FPGAs), controllers, or any other suitable computing devices or resources. Processor 138 may work, either alone or with other components depicted in FIG. 1, to provide the functionality described in the present disclosure. Memory 140 may take the form of volatile or non-volatile memory including, without limitation, magnetic media, optical media, random access memory (RAM), read-only memory (ROM), removable media, or any other suitable memory component. Memory 140 may store instructions for programs and algorithms that, when executed by processor 138, implement the functionality of controller 136 described in the present disclosure.

Among other things, controller 136 may be programmed to (or may store software in memory 140 that, when executed by processor 138, is operable to) increase or decrease the power of each light source of system 100 independently in order to set, adjust, maintain, and otherwise control the chromaticity of combined beam 101. As explained above, light beam 101 comprises a combination of constituent beams generated by the SC and monochromatic sources. Beam 101 propagates from the distal end of sleeve 117, toward collimating and condensing optics, through illuminator fiber 112, out of illumination probe 126, and into eye 128. Emitted beam 101 is perceived as a single beam of light having a particular chromaticity. The chromaticity of the combined beams may be adjusted by adjusting the power of each source.

As noted above, in certain embodiments, SC source 102 generates a white supercontinuum laser beam emitted at a pre-calibrated chromaticity. White light is often desirable for illuminating biological materials, including the eye, during surgery. Filament or gas discharge lamps, as well as LEDs, are often used to generate a white light beam in an ophthalmic illumination system, but the power and quality of the beam produced by such devices is inadequate for certain applications. And, while lasers provide very high quality light beams, they are typically confined to a very narrow spectral range. Supercontinuum lasers, however, are capable of producing a generally broadband light over a relatively wide spectral range. Supercontinuum lasers may operate by passing a generally narrow bandwidth pulsed pump beam through a dispersive, non-linear medium, such as a photonic crystal fiber. As the pump beam propagates through the dispersive, non-linear medium, a series of non-linear processes act upon the pump beam to cause spectral broadening of the initial pump beam. The result is a spectral continuum extending across the visible spectrum.

The color of light generated by each source 102, 104, 106, and 108—and combined beam 101—will at any given time have a measurable chromaticity value. The human eye has three different types of color-sensitive cone receptors, and the response of the eye to color may be described in terms of three tristimulus values defined by the International Commission on Illumination (CIE) in 1931.

Accordingly, a complete diagram of all visible colors is three-dimensional. However, as a practical matter, the concept of color can be divided into two parts—relative luminous flux (Y) and chromaticity (x, y). The CIE has defined a derivative color space specified by x, y, and Y, known as the CIE xyY color space. This scheme can be used to characterize and plot perceived colors in a two-dimensional (x,y) space known as chromaticity. FIG. 11 depicts a chromaticity diagram in accordance with this approach. The outer curved boundary of the chromaticity diagram shown in FIG. 11 represents monochromatic light—the pure hues of a single wavelength, measured in nanometers. Colors at the curved boundary of the diagram are saturated. As one moves from the curved boundary toward the center of the figure, saturation decreases. The center of the figure corresponds to white light, which becomes fully achromatic at the coordinate x=y=1/3.

As noted above, the chromaticity of a supercontinuum laser beam may be precisely calibrated at the time of manufacture to have a target chromaticity value (or range of values) within the white region of FIG. 11. At times, however, the chromaticity of a light beam emitted from a supercontinuum laser engine may not be exactly as desired at the time an ophthalmic illumination system is assembled. Moreover, due to changes in the laser engine that occur with time and use, the chromaticity of the beam generated by the SC laser may gradually change, typically shifting bluer (toward the left of FIG. 11), though possibly shifting redder (generally toward the right of FIG. 11). As the supercontinuum laser beam changes chromaticity, it will follow a particular trajectory (not necessarily a straight line) on the chromaticity diagram of FIG. 11 that depends on the individual characteristics of the source. Such chromaticity shifts may be undesirable as they risk impeding or obfuscating the surgeon's view of tissues in eye 128. Moreover, phototoxicity damage to the retina may result from exposure to blue light or white light containing a high proportion of blue light.

Accordingly, certain embodiments of system 100 offset undesirable chromaticity shifts by combining the SC laser beam with a beam of light generated by one or more monochromatic lasers, thereby setting or maintaining the chromaticity of laser beam 101 projected into eye 128 at a target value or within a target range. Because white light may be generated by mixing colors on opposite sides of a white region of FIG. 11, the chromaticity of a white beam which has shifted red, blue, or elsewhere on the chromaticity diagram of FIG. 11 may be adjusted (e.g., by controller 136) back to white by adding light from one or more monochromatic sources that lie elsewhere on the diagram. As monochromatic light is added to a supercontinuum laser beam, the chromaticity of the combined beam 101 will change depending on the power and wavelength of each constituent beam. For example, if the chromaticity of combined beam 101 shifts toward 470 nm area in blue of FIG. 11, adding monochromatic light at the opposite end of the diagram (e.g., 570 nm) at a particular power/intensity can counteract the blue shift and bring the total chromaticity back into the white region. This may be conceptualized as "balancing" chromaticity to maintain a desired target or range; chromaticity shift can be offset by adding monochromatic light opposite to the shift. Moreover, even if monochromatic light added to a beam is not exactly opposite to the unwanted chromaticity shift, it may substantially counteract chromaticity shift by bringing combined chromaticity into an acceptable range/area of FIG. 11 (though perhaps not exactly 1/3, 1/3 or the original setting). Thus, as a practical matter, a particular monochromatic light source may be useful for offsetting various chromaticity shifts.

As depicted in FIGS. 1A-1C, examples of system 100 may include one or more monochromatic laser sources. In embodiments in which the chromaticity shift of the SC source is predictable, a single monochromatic laser may be sufficient (e.g., blue to compensate for red shift, red to compensate for blue shift, etc.) as shown in FIG. 1B. In such examples, controller 136 may adjust the chromaticity of combined beam 101 over single chromaticity curve by incrementally adjusting the transmit power of the monochromatic source (e.g., between 0 and 100% power). In this manner, a target chromaticity value or range may be maintained for surgical illuminator.

For example, in certain examples a target chromaticity range for beam 101 is between 0.30<x<0.40 and 0.30<y<0.40. SC source 102 may be initially calibrated to emit a beam having chromaticity near (⅓, ⅓) and it may be known to shift red over time. Accordingly, monochromatic laser source 104 emits a blue laser beam to compensate for the red shift. In another example, SC source 102 is known to shift blue over time, and monochromatic laser source 104 emits a red laser beam to offset the chromaticity shift. One skilled in the art will appreciate that additional variations are within the scope of the disclosure.

The accuracy and precision of chromatic correction and control in a system may be improved by adding a second monochromatic laser (FIG. 1A). In such examples, controller 136 may adjust chromaticity of a combined beam 101 over a multi-dimensional chromaticity region, rather than a single chromaticity curve, by independently controlling the transmit power of two monochromatic light sources that have different spectral characteristics. For example, if it is known that the chromaticity of the SC laser beam will trend redder over time, system 100 may include both a blue and green monochromatic source to compensate for red shift with increased precision. Likewise, if it is known that the SC laser beam will trend blue over time, system 100 may include both a red and green monochromatic source to precisely maintain desired chromaticity. Again, one skilled in the art will appreciate that additional variations are within the scope of the disclosure.

Further, systems with three monochromatic laser sources (e.g., red, green, and blue) as shown in FIG. 1C can accurately and precisely compensate for a wide range of chromaticity shifts, as the addition of another monochromatic expands the multi-dimensional region over which chromaticity may be adjusted to encompass most or all of FIG. 11. Such an arrangement may be particularly useful when chromaticity migration of the SC laser is difficult to predict, or when chromaticity shifts trend one way during a part of the SC laser life cycle (e.g., toward blue) and trend another way at another part of the life cycle (e.g., toward red). Again, one skilled in the art will appreciate that additional variations are within the scope of the disclosure.

In certain examples of system 100, controller 136 may be programmed to (or may store software in memory 140 that, when executed by processor 138, is operable to) maintain, increase, or decrease the power of each monochromatic source of system 100 independently in order to control the chromaticity of combined light beam 101.

For example, if no chromaticity adjustment is needed (e.g., the SC laser beam is at the desired chromaticity) controller 136 may maintain the monochromatic sources in a no-power state (turned off). In the event monochromatic light is needed to offset a chromaticity shift, controller 136 may identify the shift, calculate an offset, and cause the appropriate monochromatic source(s) to generate a laser beam at a particular power level calculated to bring the chromaticity of beam 101 to a desired value or range. Thus, according to particular embodiments, controller 136 may precisely control the power of each monochromatic source independently to achieve incremental or continuous adjustments to the chromaticity of combined beam 101.

In certain embodiments, controller 136 may also maintain a target luminous flux. In the process of correcting for chromaticity change, where light powers from multiple monochromatic sources are either added or subtracted to maintain a given chromaticity of the combined beam 101, the resultant total luminous flux $Y_{tot}$ of the combined beam 101 (proportional to $Y_{tot}=Y_{SC}+Y_{Mono1}+Y_{Mono2}+Y_{Mono3}$) will generally change. If it is desired to ensure the actual luminous flux matches a target luminous flux at all times, regardless of chromaticity adjustments, controller 136 may execute an algorithm that senses the luminous flux relative increase $\Delta Y_{tot}/Y_{tot}$ and then adjusts the powers of all light sources (SC and monochromatic) up or down proportionally the same amount to maintain a target luminous flux.

FIGS. 1A-1C illustrate embodiments in which controller 136 is configured to automatically adjust or maintain the chromaticity of laser beam 104 by adjusting the power of sources 102-108 based on pre-stored data. For example, controller 136 may be configured to increase the power of one or more monochromatic sources 104, 106, and 108 gradually over time, based on predefined operating-time/chromaticity shift data stored in memory 140, to yield near-constant chromaticity of beam 101. Similarly, embodiments of system 100 can automatically adjust the chromaticity of beam 101 based on stored data correlating SC laser engine power or emitted laser energy with chromaticity shift. Stored data may be loaded to memory 140 at the time of manufacture, or may be loaded and/or updated via a wired or wireless communication link with a remote system.

In certain embodiments, memory 140 may store data correlating cumulative operating time of light source 102 to an expected change in (x,y) chromaticity of beam 101. Stored correlation data may, for example, associate a plurality of (x,y) chromaticity change/shift values (e.g., $\Delta x$, $\Delta y$) to particular operating time milestones, such as hour-based milestones (e.g., every 10 hours, every 50 hours, every 100 hours, etc.). Stored correlation data may additionally or alternatively associate a plurality of absolute chromaticity values (e.g., $x_1, y_1$) to particular operating time milestones. Correlation data may be based on laboratory or real-world testing of light sources. For instance, based on testing of light sources representative of SC source 102, correlative data may specify that, at 50 hours of usage of SC source 102, the expected chromaticity of the emitted beam is ($x_1, y_1$), or the expected chromaticity shift of the emitted beam is ($\Delta x_1, \Delta y_1$); at 100 hours of usage, ($x_2, y_2$) or ($\Delta x_2, \Delta y_2$); at 150 hours ($x_3, y_3$) or ($\Delta x_3, \Delta y_3$), etc.

Additionally or alternatively, memory 140 may store values specifying a power level or change in power level that will compensate for the expected change in chromaticity of beam 101. For example, memory 140 may store a plurality of $\Delta P$ values, each of which specifies a power of one or more monochromatic sources (e.g., sources 104, 106, 108) to compensate for the expected chromaticity shift of beam 101 at a given time milestone. For instance, such data may specify that, at 50 hours of usage of SC source 102, the power of monochromatic source 104 is to be increased to a particular power value or by a particular amount; at 100 hours of usage, a second increase, etc. In systems that include a plurality of monochromatic sources, the power of one or more sources may be independently adjusted at each milestone.

Based on data stored in memory 140, processor 138 may send commands to adjust the power of the monochromatic sources according to the stored data. In certain embodiments, processor 138 generates power control signals that cause each monochromatic source to emit light at a specified power value. In certain embodiments, processor 138 generates signals to separately control each monochromatic source independently. Thus, in certain embodiments, controller 136 may store software in memory 140 that, when executed by processor 138, tracks the operating time of SC light source 102, identifies when cumulative operating time reaches a predefined milestone, and automatically adjusts the power of each monochromatic light source to compensate for the expected chromaticity shift associated with that milestone, such that the chromaticity remains within a target region or at a target value. This process may be executed continuously for a plurality of milestones such that the monochromatic sources are gradually adjusted over time to maintain target chromaticity of light beam 11.

Although the above-described embodiments correlate a change in chromaticity with total operating hours, other correlative data may be used in various embodiments. For example, certain embodiments may store and implement chromaticity adjustments based on expected changes in laser engine power over time, or emitted laser energy over time.

FIG. 4 is a flow chart describing the operation of certain embodiments of system 100 which automatically adjust chromaticity based on pre-stored data. At step 1000, data associating chromaticity shifts or adjustments and operating time for light source 102 is stored in memory 140 of controller 136. For example, memory 140 may store data correlating cumulative operating time of light source 102 to an expected or average chromaticity shift of beam 104 and/or a power adjustment for monochromatic sources 104 ($\Delta P_{104}$), 106 ($\Delta P_{106}$), and 108 ($\Delta P_{108}$). In one embodiment, memory 140 may store data specifying power adjustment value(s) for 10-hour milestones:

| Cumulative Operating Time | Power Adjustment Values |
| --- | --- |
| 10 hours | $\Delta P_{104a}, \Delta P_{106a}, \Delta P_{108a}$ |
| 20 hours | $\Delta P_{104b}, \Delta P_{106b}, \Delta P_{108b}$ |
| 30 hours | $\Delta P_{104c}, \Delta P_{106c}, \Delta P_{108c}$ |
| ... | ... |

At step 1002, light (e.g., the emitted SC light beam or combined light beam 101) is generated. In certain embodiments, controller 136 may be configured to determine when SC light source 102 is emitting light in order to track usage time of the SC laser. In certain embodiments, controller 136 receives a signal when light source 102 begins emitting a SC laser beam.

At step 1004, having determined that light source 102 is emitting light, controller 136 tracks operating time of light source 102. Processor 138 and memory 140 may execute instructions to track cumulative operating time of SC light source 102, as well as the length of individual uses/sessions during which light source 102 is emitting a SC beam. Operating time may be tracked in any suitable increments, e.g., seconds, minutes, hours, etc.

At step 1006, controller 136 checks whether the tracked operating time reaches a threshold or milestone. Processor 138 may execute instructions to compare tracked operating time with predetermined chromaticity and operating time data stored in memory 140. For example, processor 138 may execute a software program which tracks operating time and periodically checks to determine whether total operating time has reached an hours-based threshold, e.g., 10 hours, 20 hours, etc. If not, the system returns to step 1002. If, however, the operating time has reached a predetermined threshold, system 100 proceeds to step 1008.

At step 1008, controller 136 determines an adjustment for each monochromatic light source in system 100. In certain embodiments, processor 138 may calculate power adjustment values for monochromatic sources 104, 106, and/or 108 based on pre-stored chromaticity shift data associated with the operating time threshold reached at step 1006. In certain embodiments, processor 138 may retrieve and/or translate pre-stored data that specifies power adjustment values for monochromatic sources 104, 106, and/or 108.

At step 1010, controller 136 generates a signal to control the power of monochromatic sources 104, 106, and/or 108 according to the determined adjustment values and to compensate for the expected chromaticity shift associated with the operating time threshold reached at step 1006. At step 1012, appropriate components of monochromatic sources 104, 106, and/or 108 are changed to achieve the power adjustment specified by the signal received from controller 136. The process may then return to step 1002.

Rather than adjusting monochromatic source power based on pre-loaded data, certain embodiments of system 100 may power levels based on real-time measurements of actual chromaticity of beam 101. FIG. 5 illustrates an embodiment in which controller 136 is configured to automatically control the chromaticity of beam 101 based on actual measured chromaticity. In addition to components and features shown in FIG. 1A, FIG. 5 includes a beam splitter 180 configured to reflect a portion of beam 101 (e.g., approximately 1%) to a chromaticity sensor module 134 coupled to controller 136. In some examples, beam splitter 180 may be a broadband, spectrally flat dichroic filter. Controller 136 may use active feedback from chromaticity sensors to ensure that the monochromatic sources 104 and 106 are powered appropriately to maintain a target chromaticity or range of the beam 101. Although filter module and beam splitter are shown positioned between the collimating lens and condensing lens, they may be arranged anywhere in optical path of light beam 104. Further, one skilled in the art will appreciate that chromaticity sensor module 134 and associated components may be integrated in like manner with the embodiments depicted in FIGS. 1B and 1C, as well.

FIG. 7 illustrates an example of chromaticity sensor module 134 in additional detail. Chromaticity sensor module 134 is configured to measure or otherwise determine the chromaticity of reflected light 132 (which is the same as the chromaticity of beam 101 as it exits collimating lens 110) and output a signal to controller 136 which indicates the chromaticity. In operation, beam splitter 180 directs reflected light 132 to a diffuser 202 (e.g., a lambertian diffuser) arranged to diffuse reflected light 132 toward a plurality of filters 204 and chromaticity sensors 206. Filters 204 and chromaticity sensors 206 may be symmetrically arranged around diffuser 202, and are configured to receive reflected light 132 and generate a signal indicating the chromaticity of light 132. Certain embodiments may include three chromaticity sensors 206a-c, each associated with a different color filter 204a-c. For example, filters 204a, 204b, and 204c may be designed to correspond to the X-bar, Y-bar, and Z-bar tristimulus function, respectively. Filters 204 are located between sensors 206 and diffuser 202, within the optical path of reflected light 132 received from diffuser 202. Accordingly, each sensor 206a-c receives reflected light 132 through an associated filter 204a-c, proportional to the color value X, Y, and Z, where the (x,y) chromaticity values are calculated by:

$$x = \frac{X}{X+Y+Z}$$
$$y = \frac{Y}{X+Y+Z}$$

Based on a measurement response to received light 132, each chromaticity sensor 206 generates a signal that indicates a detected color or chromaticity value of the filtered reflected light 132 (e.g., a chromaticity (x,y) value or tristimulus XYZ value) and outputs the signal to controller 136, which may be communicatively coupled to chromaticity sensor module 134 via wired or wireless connection. Sensors 206 may each be precalibrated using a beam of known (x,y) chromaticity to ensure the chromatic accuracy. Sensors 206 are configured to provide chromaticity signals in real-time so that controller 136 can actively adjust and maintain chromaticity of light beam 104.

Although FIG. 7 illustrates three chromaticity sensors 206, other embodiments may utilize more or fewer chromaticity sensor(s). Certain embodiments may utilize one or more chromaticity sensors configured to receive reflected light 132 directly, rather than via a diffuser and/or filter, and generate signals indicating the chromaticity of reflected slight 132 for output to controller 136.

In certain embodiments, controller 136 receives signals from one or more sensors 206a-c of chromaticity sensor module 134 and, based on the signals, control the chromaticity of light beam 104 by adjusting the power of one or more monochromatic light sources. Processor 138 and memory 140 may work together to automatically control and adjust the chromaticity of a laser beam based on a direct real-time chromaticity measurement of the laser beam 101.

In certain embodiments, memory 140 stores target chromaticity values for beam 101. For example, memory 140 may store target chromaticity (x,y) values or target tristimulus XYZ values corresponding to white for a supercontinuum laser beam 101. In certain embodiments, target values may comprise a range of values.

Signals generated by chromaticity sensor module 134 may be received by controller 136 and stored in memory 140. Processor 138 may execute software instructions to compare detected real-time chromaticity values received from sensor module 134 with target chromaticity values stored in memory 140 to calculate the difference between them, if any. In certain embodiments, processor 138 executes an algorithm to compute a difference between actual and target chromaticity values.

In the event processor 138 determines that actual chromaticity of beam 11 deviates from a target chromaticity value or range, it may additionally execute an algorithm to determine power adjustment for monochromatic sources 104, 106, and/or 108 necessary to adjust or maintain actual chromaticity of beam 101 at a target value or range. For example, processor 138 may use a Δx, Δy chromaticity value difference to determine a $\Delta P_{104}$ and $\Delta P106$, where $\Delta P_{104}$ is power level for monochromatic source 104 and $\Delta P_{106}$ is a power level for source 106 that together will cause the chromaticity of combined beam 101 exiting sleeve 117 to align with the target chromaticity value or fall within the target chromaticity range. The determined power level may be positive or negative, absolute or relative, and may comprise a change in power or an actual output power. Algorithms used to determine positional adjustment for filters 112 and 114 will be calibrated to account for the specific characteristics of the light sources and system 100, and may be based on pre-stored data. For example, processor 138 may utilize a database (e.g., a lookup table) that contains pre-stored information correlating power levels of various sources with chromaticity values/changes of combined beam 101, pre-calibrated and specific to the components of system 100.

Processor 138 may additionally generate a signal to adjust the power of monochromatic sources 104 or 106 according to determined power values. Active feedback from chromaticity sensors may be used by controller 136 to ensure that, as the power level of one or more monochromatic sources is adjusted (e.g., increased or decreased), a target chromaticity of the combined laser beam 101 is actively maintained.

FIG. 10 is a flow chart of a process for actively maintaining a target chromaticity based on real-time chromaticity measurements, according to certain embodiments. At step 1100, data identifying target chromaticity values or a target chromaticity range for light beam 101 is stored in memory 140 of controller 136. For example, memory 140 may store data specifying a specific (x,y) chromaticity value, or range of (x,y) chromaticity values (e.g., an area) in the white region of the chromaticity diagram depicted in FIG. 12.

At step 1102, light (e.g., the emitted SC light beam or combined light beam 101) is generated. In certain embodiments, controller 136 may be configured to determine when SC light source 102 is emitting light in order to track usage time of the SC laser. In certain embodiments, controller 136 receives a signal when light source 102 begins emitting a SC laser beam.

At step 1104, components of system 100 measure the actual chromaticity of light beam 101 (which may comprise the SC beam only if no monochromatic sources is turned on, or a combination of SC and monochromatic beams). In certain examples, controller 136 receives one or more signals from chromaticity sensor module 134 indicating measured chromaticity of light beam 102.

At step 1106, controller 136 determines if the measured chromaticity of light beam 101 is equal to or within range of a target chromaticity. Processor 138 and memory 140 may execute instructions to compare a target chromaticity value or range with a measured chromaticity value indicated by the signal received from sensor module 134. If it is determined that the measured chromaticity is equal to a target chromaticity value or falls within a target chromaticity range, the process returns to step 1102. If not, the process proceeds to step 1108.

At step 1108, controller 136 calculates power values for monochromatic sources 104 and/or 106 to adjust the chromaticity of beam 101 to a target value or range. For example, processor 136 may determine that the power level of source 104 and/or source 106 should be increased by $\Delta P_{104}$ and $\Delta P_{106}$, respectively, to restore the chromaticity of beam 101 to a target range. Processor 136 may be programmed to account for specific characteristics of the monochromatic sources included in system 100. That is, the particular algorithms executed by processor 136 may include constants, inputs, and variables tailored for specific monochromatic light sources. Such data may be based on laboratory or real-world testing of the light sources included in system 100.

At step 1110, controller 136 generates and sends a signal to control the power level of sources 104 and/or 106. Controller 136 may communicate a signal to cause electromechanical components of system 100 to adjust the power level according to the adjustment calculated at step 1108. At step 1012, the power of sources 104 and/or 106 is set according to the signal received from controller 136. The process may then return to step 1002.

FIG. 9 illustrates an alternative technique for combining beams generated by an SC laser and one or more monochromatic lasers. FIG. 9 includes numerous components analogous to those discussed above. However, rather than optically combining light beams using a sleeve, the system of FIG. 9 includes collimating lenses, beam expander(s), steering mirror(s), and dielectric filter(s) collectively configured to spectrally combine component light beams into a single beam 101.

In particular, the light beams generated by SC source 102 and monochromatic source 104 of FIG. 9A are separately collimated by collimating lenses 160 arranged within the beam paths, as shown. In certain embodiments, each collimating lens 160 may be identical. However, in certain embodiments it may be desirable to utilize different collimating lenses for each light source. For example, a collimating lens 160 associated with source 104 may be specially designed to collimate the monochromatic laser beam to the correct diameter for combination with the SC beam.

Additionally or alternatively, certain examples may include a fiber 114 coupled to monochromatic source 104 that has a mode field diameter at the monochromatic wavelength such that the beam exiting the fiber has the desired beam NA, as described above. Moreover, certain examples may include expanding or condensing optics to modify the collimated light beams so that they each have the same beam diameter. For instance, the collimated light beam generated by monochromatic source 104 may be transmitted through a beam expander 168 to expand the beam to the desired size. In certain embodiments, beam expander 168 may comprise two positive lenses or one negative lens and one positive lens. One or more such techniques may be used in embodiments of system 100 to ensure that each monochromatic and SC beam may be combined (by dielectric filter 170) across the entire extent of their (equal) beam area.

FIG. 9A includes a steering mirror 165 that reflects the beam of light generated by monochromatic source 104 toward a dielectric filter 170. Steering mirror 165 may, in some embodiments, comprise a fold mirror.

Because the SC beam is broadband, special consideration must be given to combine the SC beam with a monochromatic beam. The SC beam will contain some light at the monochromatic laser wavelength, though the power at that wavelength will be quite small since the total power is distributed across the entire spectrum. The SC beam may thus be combined with a monochromatic beam by passing it through a specialized filter designed to reflect narrow bands of the collimated SC laser beam into a beam dump.

In certain embodiments, dielectric filter 170 is positioned off-axis to receive each of the beams generated by SC source 102 and monochromatic source 104 (in this example, at a 45-degree angle). Dielectric filter 170, which may comprise a dichroic mirror, may be designed to reflect near-100% of light over a narrowband wavelength region centered at the monochromatic laser wavelength, but near 0% reflectance at all wavelengths outside of the narrow reflection band. Accordingly, the SC collimated beam will transmit through the filter 170 at near 100% transmittance for all wavelengths except for the narrow wavelength band of high reflectance. For this narrow wavelength band, very little of the SC collimated beam will transmit through filter 170. However, since the SC beam is broadband white, the narrow spectral notch of light that is missing from the transmitted beam amounts to a tiny percentage of the total SC laser beam power. In addition, any SC light reflected by filter 170 (into, for example, a beam dump) can be replaced by laser light from the monochromatic laser added to the SC beam.

As shown in FIG. 9A, the SC beam and monochromatic beam impinge on dielectric filter 170 at a point such that they are combined into beam 101. Dielectric filter 170 is a spectral filter that will allow the SC beam to pass through substantially unimpeded but for a narrow band of the SC beam corresponding to the wavelength of the monochromatic source, which will be reflected to beam dump 171. Moreover, dielectric filter 170 is configured to reflect near 100% of the monochromatic beam reflected by steering mirror 165. Hence, the SC beam passing through dielectric filter 170 and the monochromatic beam reflected by filter 170 are spectrally combined into a single beam 101, which may be subsequently condensed by a condensing lens 118 and transmitted into eye 128 as described above.

FIG. 10 illustrates spectral combination of SC and monochromatic beams according to certain embodiments. In this example, monochromatic source 104 is a green laser. As shown, broadband white SC light generated by the SC source impinges on dielectric filter 170. Filter 170 is designed to efficiently reflect narrow-band green light and efficiently transmit all other visible wavelengths. Accordingly, narrow-band green light from the SC source is reflected toward a beam dump (not shown), while remainder of the SC light is passed by filter 170 toward a condensing lens. In parallel, narrow-band green light from monochromatic source 104 impinges on dielectric filter 170 from another direction and is reflected toward the condensing lens. The SC beam and monochromatic beam impinge on filter 170 at a point such that the area of each wholly overlaps in combined beam 101. One skilled in the art will appreciate that FIG. 10 illustrates a principle applicable to other monochromatic light sources (e.g., red, blue) may be used together with suitable filters 170 to optically combine monochromatic laser beams with an SC laser beam according to the disclosure.

In certain embodiments, dielectric filter 170 may be composed of multiple discrete layers, each having a different refractive index. The layers may be stacked to efficiently transmit/reflect particular spectral regions, while absorbing very little. Utilizing non-absorbent materials for filter 170 may help conserve power and improve system efficiency. Dielectric filter 170 may comprise a dichroic mirror or dichroic prism.

FIG. 9B illustrates an embodiment which includes an additional monochromatic source 106 is spectrally combined with the SC laser beam in a manner analogous to monochromatic source 104, described above. Certain examples may include separate collimating lenses 160, beam expanders 168, and steering mirrors 165 for each monochromatic source to appropriately collimate, expand/resize, and direct the monochromatic beams to be combined with the SC laser beam. Each monochromatic source may be combined with the SC laser beam by separate dielectric filters 170a and 170b, each configured to reflect the portion of the SC laser beam corresponding to the monochromatic source. System 100 may include any suitable combination of red, blue, and/or green monochromatic sources and filters 170 configured to reflect the portion of the SC beam corresponding to each source. Indeed, one skilled in the art will appreciate that system 100 may include additional monochromatic sources according to the principles and examples disclosed herein, with suitable components operating in an analogous manner.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An ophthalmic illumination system, comprising:
   a supercontinuum white laser configured to emit a white supercontinuum laser beam;
   a first monochromatic light source configured to emit a first monochromatic laser beam having a first central wavelength;
   a dielectric filter configured to spectrally combine the white supercontinuum laser beam with the first monochromatic laser beam into a spectrally combined light beam, wherein the dielectric filter reflects a narrow band of the white supercontinuum laser beam that overlaps with a first monochromatic laser beam band into a beam dump;
   optics configured to receive the spectrally combined light beam comprising the white supercontinuum laser beam and the first monochromatic laser beam;
   a nano-scaled fiber optic cable configured to receive the spectrally combined light beam and deliver the spectrally combined light beam to a patient's eye; and
   a controller comprising a processor and a memory accessible to the controller configured to track an actual operating time of the supercontinuum white laser and control a chromaticity of the combined light beam by changing an output power of the first monochromatic light source;
   wherein the controller is configured to change the output power of the first monochromatic light source, independently of an output power to the supercontinuum white laser, based on predefined operating time milestone data stored in the memory accessible to the controller and the actual operating time of the supercontinuum white laser to maintain the chromaticity of the combined light beam over an operating life of the ophthalmic illumination system.

2. The ophthalmic illumination system of claim 1, further comprising a plurality of chromaticity sensors configured to measure a chromaticity of the combined light beam; and
   wherein the controller is further configured to:
   receive a signal from the chromaticity sensors indicating the measured chromaticity of the combined light beam;
   determine that the measured chromaticity is not within a target chromaticity range;
   calculate an output power adjustment for the first monochromatic light source that will modify chromaticity of the combined light beam to fall within the target chromaticity range; and
   generate a signal to change the output power of the first monochromatic light source, based on the calculated output power adjustment.

3. The ophthalmic illumination system of claim 1, further comprising:
   a sleeve optically combining the white supercontinuum laser beam with the first monochromatic laser beam.

4. The ophthalmic illumination system of claim 1, further comprising:
   a second monochromatic light source configured to emit a second monochromatic laser beam having a second central wavelength;
   wherein the combined light beam received by the optics comprises the white supercontinuum laser beam, the first monochromatic laser beam, and the second monochromatic laser beam; and
   wherein the controller is configured to control the chromaticity of the combined light beam by changing the output power of the first monochromatic light source and the second monochromatic light source.

5. The system of claim 4, wherein the controller is further configured to maintain a target luminous flux for the combined light beam.

6. The ophthalmic illumination system of claim 1, wherein the predefined operating time milestone data comprises values specifying power level changes that will compensate for expected changes in chromaticity at various cumulative operating times.

7. The ophthalmic illumination system of claim 1, wherein the predefined operating time milestone data comprises values correlating cumulative operating times with expected changes in chromaticity of the supercontinuum white laser.

8. The ophthalmic illumination system of claim 1, wherein the predefined operating time milestone data comprises values associating a plurality of absolute chromaticity values to particular cumulative operating times.

9. A method, comprising:
generating a white supercontinuum laser beam with a supercontinuum white laser;
generating a first monochromatic laser beam having a first central wavelength with a first monochromatic light source;
spectrally combining the white supercontinuum laser beam with the first monochromatic laser beam, through a dielectric filter, into a spectrally combined light beam, wherein the dielectric filter reflects a narrow band of the white supercontinuum laser beam that overlaps with a first monochromatic laser beam band into a beam dump;
receiving the combined light beam comprising the white supercontinuum laser beam and the first monochromatic laser beam with receiving optics;
delivering the spectrally combined light beam to a patient's eye through a nano-scaled fiber optic cable configured to receive the spectrally combined light beam;
tracking an actual operating time of the supercontinuum white laser; and
controlling chromaticity of the combined light beam by changing an output power of the first monochromatic light source, wherein controlling the chromaticity comprises changing the output power of the first monochromatic light source, independent of an output power to the supercontinuum white laser, based on predefined operating time milestone data and the actual operating time of the supercontinuum white laser to maintain the chromaticity of the combined light beam.

10. The method of claim 9, further comprising:
measuring the chromaticity of the combined light beam using a plurality of chromaticity sensors;
determining that the measured chromaticity is not within a target chromaticity range;
calculating an output power adjustment for the monochromatic light source that will modify chromaticity of the combined light beam to fall within the target chromaticity range; and
generating a signal to change the output power of the first monochromatic light source, based on the calculated output power adjustment.

11. The method of claim 9, further comprising optically combining the white supercontinuum laser beam with the first monochromatic laser beam with a sleeve.

12. The method of claim 9, further comprising:
generating a second monochromatic laser beam having a second central wavelength with a second monochromatic light source; and
controlling the chromaticity of the combined light beam by changing the output power of the first monochromatic light source and the second monochromatic light source; wherein the combined light beam comprises the white supercontinuum laser beam, the first monochromatic laser beam, and the second monochromatic laser beam.

13. The method of claim 12, further comprising maintaining a target luminous flux for the combined light beam.

14. The method of claim 9, wherein the predefined operating time milestone data comprises values specifying power level changes that will compensate for expected changes in chromaticity at various cumulative operating times.

15. The method of claim 9, wherein the predefined operating time milestone data comprises values correlating cumulative operating times with expected changes in chromaticity of the supercontinuum white laser.

16. The method of claim 9, wherein the predefined operating time milestone data comprises values associating a plurality of absolute chromaticity values to particular cumulative operating times.

* * * * *

UNITED STATES PATENT AND TRADEMARK OFFICE
CERTIFICATE OF CORRECTION

| | |
|---|---|
| PATENT NO. | : 11,172,560 B2 |
| APPLICATION NO. | : 15/620128 |
| DATED | : November 9, 2021 |
| INVENTOR(S) | : Smith |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 227 days.

Signed and Sealed this
Twenty-fifth Day of February, 2025

Coke Morgan Stewart
*Acting Director of the United States Patent and Trademark Office*